(12) United States Patent
Kunio

(10) Patent No.: US 12,109,056 B2
(45) Date of Patent: Oct. 8, 2024

(54) CONSTRUCTING OR RECONSTRUCTING 3D STRUCTURE(S)

(71) Applicant: Canon U.S.A., Inc., Melville, NY (US)

(72) Inventor: Mie Kunio, Boston, MA (US)

(73) Assignee: Canon U.S.A., Inc., Melville, NY (US)

( * ) Notice: Subject to any disclaimer, the term of this patent is extended or adjusted under 35 U.S.C. 154(b) by 209 days.

(21) Appl. No.: 16/990,800

(22) Filed: Aug. 11, 2020

(65) Prior Publication Data
US 2021/0077037 A1  Mar. 18, 2021

Related U.S. Application Data

(60) Provisional application No. 62/901,472, filed on Sep. 17, 2019.

(51) Int. Cl.
*A61B 6/12* (2006.01)
*A61B 5/00* (2006.01)
(Continued)

(52) U.S. Cl.
CPC .............. *A61B 6/12* (2013.01); *A61B 5/0066* (2013.01); *A61B 5/02007* (2013.01);
(Continued)

(58) Field of Classification Search
None
See application file for complete search history.

(56) References Cited

U.S. PATENT DOCUMENTS 5,357,550 A  10/1994  Asahina et al.
6,763,261 B2  7/2004  Casscells, III et al.
(Continued)

FOREIGN PATENT DOCUMENTS

JP  2009-528147 A  8/2009
JP  2013-56113 A  3/2013
(Continued)

OTHER PUBLICATIONS

S.-Y. James Chen, et al., "Quantitative Analysis of Reconstructed 3-D Coronary Arterial Tree and Intracoronary Devices", IEEE Transactions on Medical Imaging, vol. 21, No. 7, Jul. 2002, pp. 724-740.
(Continued)

*Primary Examiner* — Jason M Ip
*Assistant Examiner* — Renee C Langhals
(74) *Attorney, Agent, or Firm* — Canon U.S.A., Inc. IP Division

(57) ABSTRACT

One or more devices, systems, methods and storage mediums for optical imaging medical devices, and methods and storage mediums for use with same, for viewing, controlling, updating, and emphasizing one or more imaging modalities and/or for constructing or reconstructing 2D and/or 3D structure(s) are provided herein. One or more embodiments provide at least one intuitive Graphical User Interface (GUI), method, device, apparatus, system, or storage medium to comprehend information, including, but not limited to, molecular structure of a vessel, and to provide an ability to manipulate the vessel information and/or to construct or reconstruct 2D and/or 3D structure(s) of the vessel to improve or maximize accuracy in one or more images. In addition to controlling one or more imaging modalities, the GUI may operate for one or more applications, including, but not limited to, expansion/underexpansion (e.g., for a stent) and/or apposition/malapposition (e.g., for a stent), co-registration, and imaging.

22 Claims, 16 Drawing Sheets

(51) Int. Cl.

| | | |
|---|---|---|
| *A61B 5/02* | (2006.01) | |
| *A61B 5/107* | (2006.01) | |
| *A61B 6/00* | (2024.01) | |
| *A61B 6/46* | (2024.01) | |
| *A61B 6/50* | (2024.01) | |
| *A61B 8/08* | (2006.01) | |
| *A61B 8/12* | (2006.01) | |
| *G06T 7/00* | (2017.01) | |
| *G06T 7/30* | (2017.01) | |
| *G06T 7/70* | (2017.01) | |

(52) U.S. Cl.
CPC ............ *A61B 5/1076* (2013.01); *A61B 6/463* (2013.01); *A61B 6/465* (2013.01); *A61B 6/466* (2013.01); *A61B 6/469* (2013.01); *A61B 6/504* (2013.01); *A61B 6/507* (2013.01); *A61B 6/5217* (2013.01); *A61B 6/5247* (2013.01); *A61B 8/0891* (2013.01); *A61B 8/12* (2013.01); *G06T 7/0014* (2013.01); *G06T 7/30* (2017.01); *G06T 7/70* (2017.01); *G06T 2207/10028* (2013.01); *G06T 2207/10048* (2013.01); *G06T 2207/10064* (2013.01); *G06T 2207/10081* (2013.01); *G06T 2207/10088* (2013.01); *G06T 2207/10101* (2013.01); *G06T 2207/10116* (2013.01); *G06T 2207/10132* (2013.01); *G06T 2207/30096* (2013.01); *G06T 2207/30104* (2013.01)

(56) References Cited

U.S. PATENT DOCUMENTS

| | | |
|---|---|---|
| 7,366,376 B2 | 4/2008 | Shishkov et al. |
| 7,843,572 B2 | 11/2010 | Tearney et al. |
| 7,872,759 B2 | 1/2011 | Tearney et al. |
| 7,889,348 B2 | 2/2011 | Tearney et al. |
| 7,978,916 B2 | 7/2011 | Klingensmith et al. |
| 8,175,684 B2 | 5/2012 | Vaillant et al. |
| 8,289,522 B2 | 10/2012 | Tearney et al. |
| 8,478,387 B2 | 7/2013 | Xu |
| 8,565,859 B2 | 10/2013 | Wang et al. |
| 8,676,013 B2 | 3/2014 | Bouma et al. |
| 8,909,323 B2 | 12/2014 | Baumgart |
| 8,928,889 B2 | 1/2015 | Tearney et al. |
| RE45,534 E | 6/2015 | Huennekens et al. |
| 9,087,368 B2 | 7/2015 | Tearney et al. |
| 9,121,926 B2 | 9/2015 | Nair et al. |
| 9,138,147 B2 | 9/2015 | Schmitt et al. |
| 9,286,673 B2 | 3/2016 | Begin et al. |
| 9,292,918 B2 | 3/2016 | Zagrodsky et al. |
| 9,295,450 B2 | 3/2016 | Furuichi et al. |
| 9,301,687 B2 | 4/2016 | Kemp |
| 9,307,926 B2 | 4/2016 | Begin et al. |
| 9,332,942 B2 | 5/2016 | Jaffer et al. |
| 9,351,698 B2 | 5/2016 | Dascal et al. |
| 9,462,950 B2 | 10/2016 | Xu |
| 9,557,154 B2 | 1/2017 | Tearney et al. |
| 9,833,221 B2 | 12/2017 | Hutchins et al. |
| 9,891,044 B2 | 2/2018 | Tu et al. |
| 9,901,317 B2 | 2/2018 | Shimamura et al. |
| 10,621,748 B2 | 4/2020 | Kunio et al. |
| 10,674,985 B2 | 6/2020 | Kunio |
| 10,842,589 B2 | 11/2020 | Kunio |
| 2010/0092389 A1 | 4/2010 | Jaffer |
| 2010/0208957 A1 | 8/2010 | Chen et al. |
| 2011/0292400 A1 | 12/2011 | Fleming et al. |
| 2012/0101374 A1 | 4/2012 | Tearney et al. |
| 2014/0267038 A1* | 9/2014 | Adler ................ G06F 3/04842 345/161 |
| 2014/0275996 A1* | 9/2014 | Stigall ................ A61B 6/5247 600/424 |
| 2014/0276011 A1 | 9/2014 | Schmitt et al. |
| 2015/0131886 A1 | 5/2015 | Aben et al. |
| 2015/0250438 A1 | 9/2015 | Bozkaya et al. |
| 2015/0272442 A1 | 10/2015 | Motafakker-Fard et al. |
| 2016/0157787 A1* | 6/2016 | Merritt ............... A61B 5/02007 600/481 |
| 2016/0171711 A1 | 6/2016 | Gopinath et al. |
| 2016/0206267 A1 | 7/2016 | Shimizu et al. |
| 2016/0228097 A1 | 8/2016 | Jaffer et al. |
| 2016/0335766 A1 | 11/2016 | Ambwani et al. |
| 2017/0020392 A1 | 1/2017 | Xu |
| 2017/0024532 A1 | 1/2017 | Gopinath et al. |
| 2017/0135584 A1 | 5/2017 | Tearney et al. |
| 2018/0174490 A1* | 6/2018 | Randles ............... G09B 23/303 |
| 2018/0235713 A1* | 8/2018 | Krimsky ............... A61B 34/10 |
| 2018/0271614 A1 | 9/2018 | Kunio |
| 2019/0029623 A1 | 1/2019 | Kunio |
| 2019/0029624 A1 | 1/2019 | Kunio |
| 2019/0099080 A1 | 4/2019 | Kunio et al. |
| 2019/0102906 A1 | 4/2019 | Kunio et al. |
| 2019/0110776 A1 | 4/2019 | Yu et al. |
| 2019/0298174 A1 | 10/2019 | Watanabe |
| 2019/0339850 A1 | 11/2019 | Ho |
| 2019/0374109 A1 | 12/2019 | Wu et al. |
| 2020/0202564 A1 | 6/2020 | Kunio et al. |
| 2020/0253575 A1 | 8/2020 | Kunio |
| 2020/0390323 A1 | 12/2020 | Yamada |

FOREIGN PATENT DOCUMENTS

| | | |
|---|---|---|
| JP | 2018-196717 A | 12/2018 |
| WO | 2014/175853 A1 | 10/2014 |
| WO | 2015/045368 A1 | 4/2015 |
| WO | 2016/015052 A1 | 1/2016 |
| WO | 2016/144878 A1 | 9/2016 |
| WO | 2019/023375 A2 | 1/2019 |
| WO | 2019/023382 A1 | 1/2019 |
| WO | 2020/159984 A1 | 8/2020 |

OTHER PUBLICATIONS

Shengxian Tu, PhD, et al., "In Vivo Flow Simlulation at Coronary Bifurcation Reconstructed by Fusion of 3-Dimensional X-ray Angiography and Optical Coherence Tomography", Images and Case Reports in Interventional Cardiology, Apr. 2013, pp. e15-e17.

Morton Kern, MD, "Comparing FFR Tools: New Wires and a Pressure Microcatheter", CathLab Digest, vol. 24, Issue 6, May 2016, pp. 1-7, www.cathlabdigest.com/article/Comparing-FFR-Tools-New-Wires-Pressure-Microcatheter (retrieved Aug. 4, 2020).

Shengxian Tu, PhD, et al., "Diagnostic Accuracy of Fast Computational Approaches to Derive Fractional Flow Reserve From Diagnostic Coronary Angiography: The International Multicenter FAVOR Pilot Study", JACC: Cardiovascular Interventions, vol. 9, No. 19, Oct. 2016, pp. 2024-2035.

Paul D. Morris, PhD, et al., "Fast Virtual Fractional Flow Reserve Based Upon Steady-State Computational Fluid Dynamics Analysis—Results from the VIRTU-Fast Study", JACC: Basic to Translational Science, vol. 2, No. 4, Aug. 2017, pp. 434-446, https://www.ncbi.nlm.nih.gov/pmc/articles/PMC5582193/ (Retrieved on Jul. 29, 2020).

Morton J. Kern, MD, "Noninvasive Angiographic-Derived FFR: Is Wireless Physiology Coming to Your Cath Lab Soon?", Cath Lab Digest, vol. 16, Issue 2, Feb. 2018, pp. 1-6, https://www.cathlabdigest.com/article/Noninvasive-Angiographic-Derived-FFR-Wireless-Physiology-Coming-Your-Cath-Lab-Soon (Retrieved on Jul. 29, 2020).

Ryota Fukuoka, MD, "Diagnostic performance of On-site CT-derived FFR—Comparison with fusion myocardial perfusion and invasive FFR", Powerpoint Presentation, TCT 2018 Conference, Sep. 21, 2018, pp. 1-25.

Shengxian Tu, PHD, FACC, FESC, et al., "Diagnostic Accuracy of Fast Computational Approaches to Derive Fractional Flow Reserve from Optical Coherence Tomography", Powerpoint Presentation, TCT Conference 2018, Sep. 2018, pp. 1-26.

Morton J. Kern, MD, "FFR/NHPR (eg, iFR) Caveats: Real World Challenges—Left Main, Diffuse Disease, CTOs", Powerpoint Presentation, Oct. 2018, pp. 1-22.

(56) References Cited

OTHER PUBLICATIONS

G.P.M. Prause, et al., "Semi-automated segmentation and 3-D reconstruction of coronary trees: Biplane angiography and intravascular ultrasound data fusion", Proceedings of SPIE, IEEE, XP002914810, vol. 2709, Feb. 1996, pp. 82-92.
Klein, H. M., et al., "3D-Surface Reconstruction of Intravascular Ultrasound Images Using Personal Computer Hardware and a Motorized Catheter Control", Cardiovascular Interventional Radiology, vol. 15, Mar.-Apr. 1992, pp. 97-101.
Laban, M., et al., "ANGUS: A New Approach to Three-Dimensional Reconstruction of Coronary Vessels by Combined Use of Angiography and Intravascular Ultrasound", Computers in Cardiology, IEEE, Oct. 1995, pp. 325-238.
Shekhar, R., et al., "Fusion of Intravascular Ultrasound and Biplane Angiography for Three-Dimensional Reconstruction of Coronary Arteries", IEEE, Computers in Cardiology, Sep. 1996, pp. 5-8.
Wahle, A., et al., "Geometrically Correct 3-D Reconstruction of Intravascular Ultrasound Images by Fusion with Biplane Angiography—Methods and Validation", IEEE Transactions on Medical Imaging, vol. 18, No. 8, Aug. 1999, pp. 686-699.
Wahle, A., et al., "Fusion of Angiography and Intravascular Ultrasound in vivo: Establishing the Absolute 3-D Frame Orientation", IEEE Transactions on Biomedical Engineering, vol. 46, No. 10, Oct. 1999, pp. 1176-1180.
Hoffmann, K. R., et al., "Biplane X-ray angiograms, intravascular ultrasound, and 3D visualization of coronary vessels", International Journal of Cardiac Imaging, vol. 15, Dec. 1999, pp. 495-512.
Subramanian, K. R., et al., "Accurate 3D reconstruction of complex blood vessel geometries from intravascular ultrasound images: in vitro study", Journal of Medical Engineering & Technology, vol. 24, No. 4, Jul./Aug. 2000, pp. 131-140.
Slager, C. J., et al., "True 3-Dimensional Reconstruction of Coronary Arteries in Patients by Fusion of Angiography and IVUS (ANGUS) and Its Quantitative Validation", vol. 102, No. 5, Aug. 2000, pp. 511-516.
Sarwal, A., et al., "Three dimensional reconstruction of coronary arteries from two views", Computer Methods and Programs in Biomedicine, vol. 65, Issue 1, Apr. 2001, pp. 25-43, ISSN: 0169-2607.
Coskun, A. U., et al., "Reproducibility of Coronary Lumen, Plaque, and Vessel Wall Reconstruction and of Endothelial Shear Stress Measurements In Vivo in Humans", Catheterization and Cardiovascular Interventions, vol. 60, Sep. 2003, pp. 67-78.
Bourantas, C.V., et al., "A method for 3D reconstruction of coronary arteries using biplane angiography and Intravascular ultrasound images", Computerized Medical Imaging and Graphics, vol. 29, Nov. 2005, pp. 597-606.
Blondel, C., et al., "Reconstruction of Coronary Arteries From a Single Rotational X-Ray Projection Sequence", IEEE Transactions on Medical Imaging, vol. 25, No. 5, May 2006, pp. 653-663.
Giannoglou, G. D., et al., "In-vivo validation of spatially correct three-dimensional reconstruction of human coronary arteries by integrating intravascular ultrasound and biplane angiography", Diagnostic methods, Coronary Artery Disease, vol. 17, No. 6, Sep. 2006, pp. 533-543.
Zhang, W., et al., "3D Vessel Tree Reconstruction from Rotational C-arm Projections by Multi-view Stereo Reconstruction", APCMBE 2008: 7th Asian-Pacific Conference on Medical and Biological Engineering, IFMBE Proceedings, vol. 19, Apr. 2008, pp. 434-441, ISBN: 1680-0737.
Bourantas, C. V., et al., "ANGIOCARE: An Automated System for Fast Three-Dimensional Coronary Reconstruction by Integrating Angiographic and Intracoronary Ultrasound Data", Catheterization and Cardiovascular Interventions, vol. 72, Apr. 2008, pp. 166-175.
Kang, D., et al., "Three-Dimensional Blood Vessel Quantification via Centerline Deformation", IEEE Transactions on Medical Imaging, vol. 28, No. 3, Mar. 2009, pp. 405-414.

Yang, J., et al., "Novel Approach for 3-D Reconstruction of Coronary Arteries from Two Uncalibrated Angiographic Images", IEEE Transactions on Image Processing, vol. 18, No. 7, Jul. 2009, pp. 1563-1572.
Tu, S., et al., "Assessment of obstruction length and optimal viewing angle from biplane X-ray angiograms", Int. J. Cardiovasc. Imaging, vol. 26, No. 1, Jan. 2010, pp. 5-17.
Van Der Giessen, A., et al., "3D fusion of intravascular ultrasound and coronary computed tomography for in-vivo wall shear stress analysis: a feasibility study", Int. J. Cardiovasc. Imaging, vol. 26, No. 7, Oct. 2010, pp. 781-796.
Tu, S., et al., "Fusion of 3D QCA and IVUS/OCT", International Journal of Cardiovascular Imaging, vol. 27, Issue 2, Feb. 2011, pp. 197-207.
Ellwein, L.M., et al., "Optical Coherence Tomography for Patient-specific 3D Artery Reconstruction and Evaluation of Wall Shear Stress in a Left Circumflex Coronary Artery", Cardiovascular Engineering and Technology, vol. 2, No. 3, Sep. 2011, pp. 212-227.
Cardenes, R., et al., "3D Reconstruction of Coronary Arteries From Rotational X-Ray Angiography", IEEE, May 2012, pp. 618-621.
Kraus, M.F., et al., "Motion correction in optical coherence tomography vols. on a per A-scan basis using orthogonal scan patterns", Bio. Med. Optics Express, vol. 3, No. 6, Jun. 1, 2012, pp. 1182-1199.
Athanasiou, L.S., et al., "3D Reconstruction of Coronary Arteries using Frequency Domain Optical Coherence Tomography Images and Biplane Angiography", IEEE, Aug. 2012 (four pages).
Rivest-Hénault, D., et al., "Nonrigid 2D/3D Registration of Coronary Artery Models With Live Fluoroscopy for Guidance of Cardiac Interventions", IEEE Transactions on Medical Imaging, vol. 31, No. 8, Aug. 2012, pp. 1557-1572.
Tu, S., et al., "In vivo comparison of arterial lumen dimensions assessed by co-registered three-dimensional (3D) quantitative coronary angiography, intravascular ultrasound and optical coherence tomography", Int. J. Cardiovasc. Imaging, vol. 28, No. 6, Jan. 2012, pp. 1315-1327.
Khaleel, H. H., et al., "A Review paper of 3D Surface Reconstruction of Coronary Arteries From Cardiovascular Angiography", 2012 International Conference on Advanced Computer Science Applications and Technologies (Acsat), pp. 419-435, Nov. 2012, DOI: DOI 10.1109/Acsat.2012.13.
Kumar, R.P., et al., "3D multiscale vessel enhancement based centerline extraction of blood vessels", Medical Imaging 2013: Image Processing, Proc. SPIE vol. 8669, Mar. 2013 (ten pages).
Bourantas, C. V., et al., "A new methodology for accurate 3-dimensional coronary artery reconstruction using routine intravascular ultrasound and angiographic data: implications for widespread assessment of endothelial shear stress in humans", Euro Intervention, vol. 9, Apr. 2013, pp. 582-593.
Tu, S., et al., "In Vivo Flow Simulation at Coronary Bifurcation Reconstructed by Fusion of 3-Dimensional X-ray Angiography and Optical Coherence Tomography", Circ. Cardiovasc. Interv., vol. 6, No. 2, Apr. 2013, pp. e15-e17 (5 pages included).
Timmins, L. H., et al., "Framework to Co-register Longitudinal Virtual Histology-Intravascular Ultrasound Data in the Circumferential Direction", IEEE Transactions on Medical Imaging, vol. 32, No. 11, Nov. 2013, pp. 1989-1996.
Bourantas, C. V., et al., "Bioresorbable vascular scaffold treatment induces the formation of neointimal cap that seals the underlying plaque without compromising the luminal dimensions: a concept based on serial optical coherence tomography data", Euro Intervention, Oct. 2014, pp. 1-16.
Hebsgaard, L., et al., "Co-registration of optical coherence tomography and X-ray angiography in percutaneous coronary intervention. The Does Optical Coherence Tomography Optimize Revascularization (DOCTOR) fusion study" International Journal of Cardiology, vol. 182, Mar. 2015, pp. 272-278.
Dehkordi, et al., "Extraction of the Best Frames in Coronary Angiograms for Diagnosis and Analysis", J Med Signals, Sens., vol. 6, No. 3, Jul.-Sep. 2016, pp. 150-157 (14 pages included with figures).
Horsley, E., "Imaging for the Future; Intravascular Optical Coherence Tomography", Sep. 10, 2016; from https://www.slideshare.net/

(56) References Cited

OTHER PUBLICATIONS

ErnestHorsley/coronary-optical-coherence-tomography-oct-angio-coregistration-acr-and-metal-stent-optimisation-mso-softwarefrom (42 pages).

\* cited by examiner

CONSTRUCTING OR RECONSTRUCTING 3D STRUCTURE(S)

CROSS-REFERENCE TO RELATED APPLICATION(S)

This application relates, and claims priority, to U.S. Patent Application Ser. No. 62/901,472, filed Sep. 17, 2019, the entire disclosure of which is incorporated by reference herein in its entirety.

FIELD OF THE INVENTION

This present disclosure generally relates to computer imaging and/or to the field of optical imaging, particularly to devices/apparatuses, systems, methods, and storage mediums for constructing or reconstructing three-dimensional (3D) structure(s) and/or for using one or more imaging modalities, such as, but not limited to, angiography, Optical Coherence Tomography (OCT), Multi-modality OCT (MM-OCT), near-infrared fluorescence (NIRAF), OCT-NIRAF, etc. Examples of OCT applications include imaging, evaluating and diagnosing biological objects, such as, but not limited to, for gastro-intestinal, cardio and/or ophthalmic applications, and being obtained via one or more optical instruments, such as, but not limited to, one or more optical probes, one or more catheters, one or more endoscopes, one or more capsules, and one or more needles (e.g., a biopsy needle). One or more devices, systems, methods and storage mediums for characterizing, examining and/or diagnosing, and/or measuring a target, sample, or object in application(s) using an apparatus or system that uses and/or controls one or more imaging modalities are discussed herein.

BACKGROUND OF THE INVENTION

Fiber optic catheters and endoscopes have been developed to access to internal organs. For example in cardiology, Optical Coherence Tomography (OCT) has been developed to see depth resolved images of vessels with a catheter. The catheter, which may include a sheath, a coil and an optical probe, may be navigated to a coronary artery.

OCT is a technique for obtaining high-resolution cross-sectional images of tissues or materials, and enables real time visualization. The aim of the OCT techniques is to measure the time delay of light by using an interference optical system or interferometry, such as via Fourier Transform or Michelson interferometers. A light from a light source delivers and splits into a reference arm and a sample (or measurement) arm with a splitter (e.g., a beamsplitter). A reference beam is reflected from a reference mirror (partially reflecting or other reflecting element) in the reference arm while a sample beam is reflected or scattered from a sample in the sample arm. Both beams combine (or are recombined) at the splitter and generate interference patterns. The output of the interferometer is detected with one or more detectors, such as, but not limited to, photodiodes or multi-array cameras, in one or more devices, such as, but not limited to, a spectrometer (e.g., a Fourier Transform infrared spectrometer). The interference patterns are generated when the path length of the sample arm matches that of the reference arm to within the coherence length of the light source. By evaluating the output beam, a spectrum of an input radiation may be derived as a function of frequency. The frequency of the interference patterns corresponds to the distance between the sample arm and the reference arm. The higher frequencies are, the more the path length differences are. Single mode fibers may be used for OCT optical probes, and double clad fibers may be used for fluorescence and/or spectroscopy.

A multi-modality system such as an OCT, fluorescence, and/or spectroscopy system with an optical probe is developed to obtain multiple information at the same time. During vascular diagnosis and intervention procedures, such as Percutaneous Coronary Intervention (PCI), users of optical coherence tomography (OCT) sometimes have difficulty understanding the tomography image in correlation with other modalities because of an overload of information, which causes confusion in image interpretation.

Physiological assessment of coronary artery disease, such as fractional flow reserve (FFR) and instantaneous wave-free ratio (iFR), is one of the important tools to decide whether patients should undergo percutaneous coronary intervention (PCI) and/or to evaluate the procedural success of PCI. However, current invasive measurement technology requires injection of a vasodilator prior to measurement and/or may not have same accuracy between physicians due to technical difficulties. Computational fluid dynamics (CFD)-based technology may be used after imaging with non-invasive methods, like computed tomography angiography (CTA), and after performing reconstruction. CFD-based technology requires a 3D structure of the vessel with the boundary condition and initial condition of the blood flow rate. The 3D structure of the vessel may be reconstructed from computerized tomography (CT), angiography or CTA, or intravascular imaging (intravascular ultrasound (IVUS), optical coherence tomography (OCT), etc.). CT-based technology may be used as a screening tool. However, CT-based technology is not used as a tool during the PCI procedure. Angiography-based technology may be a tool in a cath lab. However, due to low resolution of angiography, the 3D reconstruction is not as accurate as CT. Unfortunately, CFD requires some time to process, and, even in a case where CFD would be used, the subject time is added as well as the time needed to perform any reconstruction process. In view of the additional time required by CFD, any use of CFD makes a whole procedure not real-time applicable.

Accordingly, it would be desirable to provide at least one imaging or optical apparatus/device, system, method, and storage medium for using, controlling, and/or emphasizing one or more imaging modalities, for example, by using one or more processes or interfaces to obtain a more accurate 3D structure of an object to be examined (e.g., a vessel), for example, that considers side branch location relative to a curvature and plaque information (e.g., as a boundary condition), and/or to obtain more accurate flow pattern and/or simulation results, which provides better pressure simulation results.

SUMMARY OF THE INVENTION

Accordingly, it is a broad object of the present disclosure to provide imaging (e.g., OCT, NIRAF, etc.) apparatuses, systems, methods and storage mediums for using and/or controlling multiple imaging modalities. It is also a broad object of the present disclosure to provide OCT devices, systems, methods and storage mediums using an interference optical system, such as an interferometer (e.g., spectral-domain OCT (SD-OCT), swept-source OCT (SS-OCT), multimodal OCT (MM-OCT), etc.).

One or more embodiments provide at least one intuitive Graphical User Interface (GUI), method, device, apparatus, system, or storage medium to comprehend information, including, but not limited to, molecular structure of an object (e.g., a vessel), and to provide an ability to manipulate or to construct/reconstruct a 3D structure (e.g., of or based on the vessel information).

One or more embodiments may improve 3D structure construction or reconstruction by one or more of: determining an in-plane orientation of an intravascular image frame; considering a side branch location relative to a vascular curvature; and considering the plaque type and its location for boundary condition. For example, in one or more embodiments, improving or optimizing accuracy of 3D structure(s) of an object (e.g., of a vessel) may help a physician or clinician evaluate a lesion physiologically with CFD-based method(s) (e.g., one or more methods of the present disclosure may use 2D or 3D results and/or 2D or 3D structure(s) and may calculate the FFR; one or more methods of the present disclosure may calculate the FFR and provide information on treatment option(s) for the treatment of stenosis and/or another medical condition; one or more methods of the present disclosure may employ information on 2D or 3D results and/or structure(s) for the object in order to construct a CFD model for the object; one or more methods of the present disclosure may employ CFD to calculate one or more pressures and to have or obtain the FFR; one or more methods of the present disclosure may calculate FFR and may automatically decide or a user may decide to treat or not treat stenosis and/or other condition; one or more methods of the present disclosure may use FFR in real-time; one or more methods of the present disclosure may calculate pressure(s) and may include a lamp parameter/circuit analog model; one or more embodiments of the present disclosure may include an OCT FFR method that uses anatomic information (e.g., a volume of a vessel, any other anatomic information discussed in the present disclosure, etc.); etc.), to plan PCI during a procedure, and to assess procedural success of the PCI more accurately.

One or more embodiments of an image processing apparatus may include: one or more processors that operate to: obtain an angiography image of an object; obtain an intravascular image at an acquisition location that is within at least a portion of the object, wherein the angiography image is obtained before the obtaining of the intravascular image, after the obtaining of the intravascular image, or simultaneously with the obtaining of the intravascular image; determine the acquisition location of the intravascular image in the object within the angiography image; determine an in-plane orientation of the intravascular image based on the intravascular image and the angiography image; and register the intravascular image to the angiography image based on the determined acquisition location and the determined in-plane orientation.

In one or more embodiments, the one or more processors may further operate to one or more of the following: co-register the obtained angiography image and the obtained intravascular image; determine whether a Percutaneous Coronary Intervention (PCI) is needed for the object and/or patient; in a case where it is determined that the object needs the PCI, perform the PCI, obtain one or more additional angiography and/or intravascular images, and perform the determining of the acquisition location, the determining of the in-plane orientation, and the registering for the one or more additional angiography and/or intravascular images, or, in a case where it is determined that the object does not need the PCI, save the images; in a case where the PCI is to be performed, plan the PCI; in a case where the PCI is performed, assess or evaluate procedural success of the PCI; evaluate the physiology of the object; and in a case where the object is a vessel or blood vessel, evaluate the physiology of the vessel and/or a lesion of the vessel. In one or more embodiments, the one or more processors may further operate to one or more of the following: co-register the obtained angiography image and an obtained one or more Optical Coherence Tomography (OCT) or Intravascular Ultrasound (IVUS) images or frames; obtain information from the one or more OCT or IVUS images or frames of one or more of the following: a plaque type and its location, a lumen shape and/or size, and one or more side branches of the object, wherein the object is a blood vessel; determine the in-plane orientation of each OCT or IVUS frame using information of a curvature, the one or more side branches, and the lumen size based on information from both the one or more OCT or IVUS images or frames and the angiography image or images; construct or reconstruct a three-dimensional (3D) structure of the object; and use the constructed or reconstructed 3D structure for one or more of visualization, Percutaneous Coronary Intervention (PCI) planning, PCI performance, and physiological assessment. In one or more embodiments, the one or more processors may further operate to one or more of the following: determine OCT or IVUS in-plane orientation relative to a co-registration path using side branch location information relative to a main branch or predetermined branch of the blood vessel; display an option to perform the construction or reconstruction of the 3D structure on a display of the device; display buttons, choices or options to perform the in-plane orientation determination automatically or manually; in a case where a manual in-plane orientation determination is selected, receive an input rotation angle that is used to place the OCT or IVUS frame on the co-registration path or co-registration path plane, and receive an input OCT or IVUS frame number to change the display to the input OCT or IVUS frame for performance of the in-plane orientation determination; and in a case where an automatic in-plane orientation determination is selected, perform the in-plane orientation determination automatically based on the intravascular image and the angiography image.

In one or more embodiments, the object may be a blood vessel, and the acquisition location may be a region that is diseased and/or is a region that a physician(s), clinician(s) or other user(s) of the apparatus is/are considering for further assessment. In one or more embodiments, one or more processors may operate to determine the in-plane orientation of the intravascular image with respect to a blood vessel in the intravascular image. In one or more embodiments, the one or more processors may operate to determine the in-plane orientation of the intravascular image with respect to a pullback direction at the determined acquisition location.

In one or more embodiments, one or more processors may further operate to one or more of the following: (i) display an image for each of multiple imaging modalities on a display, wherein the multiple imaging modalities include two or more of the following: a tomography image; an Optical Coherence Tomography (OCT) image; a fluorescence image; a near-infrared fluorescence (NIRAF) image; a near-infrared fluorescence (NIRAF) in a predetermined view (e.g., a carpet view, an indicator view, etc.); a three-dimensional (3D) rendering; a 3D rendering of a vessel; a 3D rendering of a vessel in a half-pipe view or display; a 3D rendering of the object; a lumen profile; a lumen diameter display; a longitudinal view; computer tomography (CT); Magnetic Resonance Imaging (MRI); Intravascular Ultrasound (IVUS); an X-ray image or view; and an angiography view; (ii) display an image for each of multiple imaging modalities on a display, wherein the multiple imaging modalities include three or more of the following: a tomography image; an Optical Coherence Tomography (OCT) image; a fluorescence image; a near-infrared fluorescence (NIRAF) image; a near-infrared fluorescence (NIRAF) in a predetermined view (e.g., a carpet view, an indicator view, etc.); a three-dimensional (3D) rendering; a 3D rendering of a vessel; a 3D rendering of a vessel in a half-pipe view or display; a 3D rendering of the object; a lumen profile; a lumen diameter display; a longitudinal view; computer tomography (CT); Magnetic Resonance Imaging (MRI); Intravascular Ultrasound (IVUS); an X-ray image or review; and an angiography view; and (iii) change or update the displays for each of the multiple imaging modalities based on the in-plane orientation information and/or based on a request to update or change the in-plane orientation.

In one or more embodiments, one or more processors may further operate to one or more of the following: (i) receive information for an interventional device to be used for a Percutaneous Coronary Intervention (PCI); and (ii) in a case where the interventional device is a stent, perform one or more of: detecting stent expansion or underexpansion, detecting stent apposition or malapposition, performing co-registration, performing imaging, displaying a notification regarding the detected stent expansion or underexpansion, and displaying a notification regarding the detected stent apposition or malapposition.

In one or more embodiments, one or more processors may employ computational fluid dynamics (CFD) using a two-dimensional (2D) and/or three-dimensional (3D) structure or structures and/or results of the object that is constructed or reconstructed. For example, one or more embodiments of the present disclosure may employ information on 2D or 3D results and/or structure(s) for the object in order to construct a CFD model for the object.

One or more embodiments may include or further include a touch screen, wherein one or more processors further operate to one or more of the following: detect a selected region of interest, via an input received through or with the touch screen; detect an input update request via a single press/touch and drag with a finger or tool of a user over an area of the touch screen to change or update one or more of the views or images; detect an input update request via two simultaneous touch points made on the at least one imaging modality view or image and redraw the image of the at least one imaging modality such that a control bar or tool having two handles defines the redrawn image where both of the two handles align near or on an arc of the redrawn image based on the two touch points, and calculate and update the new orientation/position of the at least one imaging modality image or view based upon a release of the two touch points; and detect two simultaneous touch points, made by fingers or tools of the user, made on the at least one imaging modality showing a tomographic image or an Optical Coherence Tomography (OCT) image, where the fingers or the tools are held in place, and the two touch points are swept around the tomographic image or the OCT image in a circular motion that moves a rotational control bar displayed on the at least one imaging modality, and calculate and update the new orientation/position of the at least one imaging modality image or view based upon a release of the two touch points.

In one or more embodiments of the present disclosure, at least one method for constructing or reconstructing a 3D structure of an object (e.g., of a vessel) (and/or one or more storage mediums having instructions that operate to cause a processor or processors to perform the at least one method), may include: obtaining an angiography image of an object; obtaining an intravascular image at an acquisition location that is within at least a portion of the object, wherein the angiography image is obtained before the obtaining of the intravascular image, after the obtaining of the intravascular image, or simultaneously with the obtaining of the intravascular image; determining the acquisition location of the intravascular image in the object within the angiography image; determining an in-plane orientation of the intravascular image based on the intravascular image and the angiography image; and registering the intravascular image to the angiography image based on the determined acquisition location and the determined in-plane orientation.

The present disclosure describes a means to allow OCT users to focus on the area of interest in one or more imaging modalities, such as, but not limited to, a tomography image, fluorescence information, near-infrared fluorescence (NIRAF) information in a predetermined view (e.g., a carpet view, an indicator view, etc.), three-dimensional (3D) rendering of an object (e.g., a coronary artery, a vessel, etc.) in one or more views (e.g., in a half pipe display, in a lumen diameter display, in a longitudinal view, in an angiography view, in an indicator view, etc.). As described below, one or more of the displayed imaging modalities may be controlled by any one of several control bars or features, which allow the user to change and update each display and to construct or reconstruct accurate or more accurate 3D structure(s) when appropriate. This allows the users to get a full view of the structural vessel information using one or more modalities and also allows configurability of the function for more targeted focus and/or accurate or improved construction or reconstruction of 3D structure(s).

When the user obtains an intravascular image at a location within the object, that specific portion of the object may be at a predetermined location based on prior angiographic images or other information.

In one or more embodiments of the present disclosure, an accurate (or a more accurate (in comparison to when not employing the one or more features of the present disclosure)) 3D structure of an object (e.g., a vessel) may be reconstructed by having both an OCT-NIRAF image or view and one (1) view of an angiography image because the embodiment may consider one or more of the following: (a) side branch location relative to the curvature (e.g., based on information from OCT-angiography co-registration), (b) an accurate or more accurate OCT frame in-plane orientation relative to a co-registration path (e.g., from OCT-angiography co-registration), and/or (c) plaque information (from OCT and/or NIRAF). One or more embodiments may involve a 3D construction or reconstruction result from OCT and/or IVUS and two (2) views of angiography image(s). One or more further embodiments may involve a 3D construction or reconstruction result from OCT and/or NIRAF and two (2) views of angiography image(s). While more than one angiography image may be used in one or more embodiments of the present disclosure, at least one angiography image is used in one or more embodiments. In one or more embodiments, a physician or clinician may improve or optimize an angle of angiography for the one or more angiography images (e.g., to avoid foreshortening of an object (e.g., a vessel) in the viewing angle).

The following paragraphs describe certain explanatory embodiments. Other embodiments may include alternatives, equivalents, and modifications. Additionally, the explanatory embodiments may include several novel features, and a particular feature may not be essential to some embodiments of the devices, systems, and methods that are described herein.

According to other aspects of the present disclosure, one or more additional devices, one or more systems, one or more methods and one or more storage mediums using OCT and/or other imaging modality technique(s) to construct/reconstruct 3D structure(s) are discussed herein. Further features of the present disclosure will in part be understandable and will in part be apparent from the following description and with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein.

DETAILED DESCRIPTION OF THE PRESENT INVENTION

One or more devices, systems, methods and storage mediums for characterizing tissue, or an object, using one or more imaging techniques or modalities (such as, but not limited to, OCT, fluorescence, NIRAF, etc.) are disclosed herein. Several embodiments of the present disclosure, which may be carried out by the one or more embodiments of an apparatus, system, method and/or computer-readable storage medium of the present disclosure are described diagrammatically and visually in FIGS. 1A through 12.

Turning now to the details of the figures, imaging modalities may be displayed in one or more ways as discussed herein. One or more displays discussed herein may allow a user of the one or more displays to use, control and/or emphasize multiple imaging techniques or modalities, such as, but not limited to, OCT, NIRAF, etc., and may allow the user to use, control, and/or emphasize the multiple imaging techniques or modalities synchronously.

Figure 1A:
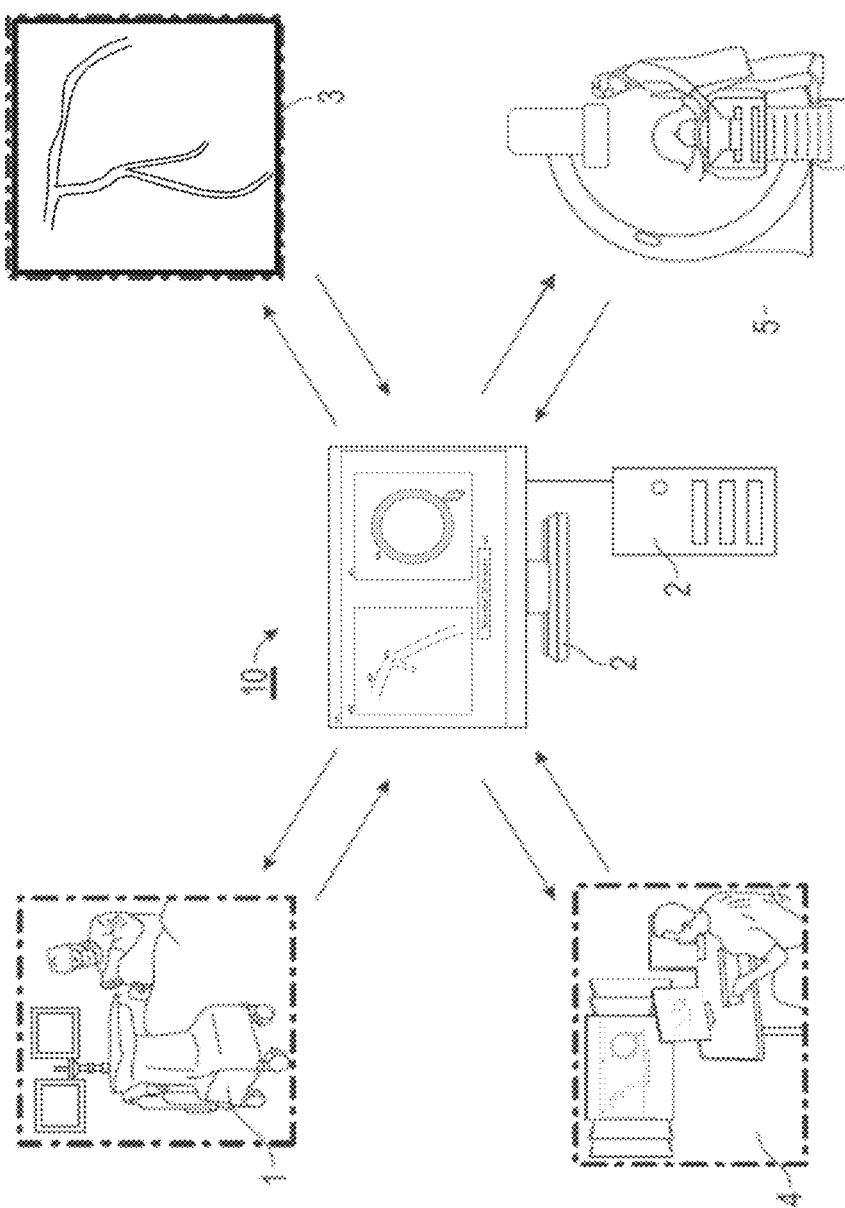
FIG. 1A is a schematic diagram showing at least one embodiment of a system that may be used for performing one or multiple imaging modality viewing and control in accordance with one or more aspects of the present disclosure.

As shown diagrammatically in FIG. 1A, one or more embodiments for visualizing, emphasizing and/or controlling one or more imaging modalities for constructing and/or reconstructing 3D structure(s) of the present disclosure may be involved with one or more predetermined or desired procedures, such as, but not limited to, medical procedure planning and performance (e.g., PCI as aforementioned). For example, the system 2 may communicate with the image scanner 5 (e.g., a CT scanner, an X-ray machine, etc.) to request information for use in the medical procedure (e.g., PCI) planning and/or performance, such as, but not limited to, bed positions, and the image scanner 5 may send the requested information along with the images to the system 2 once a clinician uses the image scanner 5 to obtain the information via scans of the patient. In some embodiments, one or more angiograms 3 taken concurrently or from an earlier session are provided for further planning and visualization. The system 2 may further communicate with a workstation such as a Picture Archiving and Communication System (PACS) 4 to send and receive images of a patient to facilitate and aid in the medical procedure planning and/or performance. Once the plan is formed, a clinician may use the system 2 along with a medical procedure/imaging device 1 (e.g., an imaging device, an OCT device, an IVUS device, a PCI device, an ablation device, a 3D structure construction or reconstruction device, etc.) to consult a medical procedure chart or plan to understand the shape and/or size of the targeted biological object to undergo the imaging and/or medical procedure. Each of the medical procedure/imaging device 1, the system 2, the locator device 3, the PACS 4 and the scanning device 5 may communicate in any way known to those skilled in the art, including, but not limited to, directly (via a communication network) or indirectly (via one or more of the other devices such as 1 or 5, or additional flush and/or contrast delivery devices; via one or more of the PACS 4 and the system 2; via clinician interaction; etc.).

In medical procedures, improvement or optimization of physiological assessment is preferable to decide a course of treatment for a particular patient. By way of at least one example, physiological assessment is very useful for deciding treatment for cardiovascular disease patients. In a catheterization lab, for example, physiological assessment may be used as a decision-making tool—e.g., whether a patient should undergo a PCI procedure, whether a PCI procedure is successful, etc. While the concept of using physiological assessment is theoretically sound, physiological assessment still waits for more adaption and improvement for use in the clinical setting(s). This situation may be because physiological assessment may involve adding another device and medication to be prepared, and/or because a measurement result may vary between physicians due to technical difficulties. Such approaches add complexities and lack consistency. Therefore, one or more embodiments of the present disclosure may employ CFD-based physiological assessment that may be performed from imaging data to eliminate or minimize technical difficulties, complexities and inconsistencies during the measurement procedure (e.g., one or more methods of the present disclosure may use 2D or 3D results and/or 2D or 3D structure(s) and may calculate the FFR; one or more methods of the present disclosure may calculate the FFR and provide information on treatment option(s) for the treatment of stenosis and/or another medical condition; one or more methods of the present disclosure may employ information on 2D or 3D results and/or structure(s) for the object in order to construct a CFD model for the object; one or more methods of the present disclosure may employ CFD to calculate one or more pressures and to have or obtain the FFR; one or more methods of the present disclosure may calculate FFR and may automatically decide or a user may decide to treat or not treat stenosis and/or other condition; one or more methods of the present disclosure may use FFR in real-time; one or more methods of the present disclosure may calculate pressure(s) and may include a lamp parameter/circuit analog model; one or more embodiments of the present disclosure may include an OCT FFR method that uses anatomic information (e.g., a volume of a vessel, any other anatomic information discussed in the present disclosure, etc.); etc.). To obtain accurate physiological assessment, accurate 3D structure of the vessel needs to be reconstructed from the imaging data.

In at least one embodiment of the present disclosure, a method may be used to provide more accurate 3D structure(s) compared to using only one imaging modality. In one or more embodiments, a combination of multiple imaging modalities may be used via adding another specific imaging condition for physiological assessment. In at least one further embodiment example, a method of 3D reconstruction without adding any imaging requirements or conditions may be employed. One or more methods of the present disclosure may use intravascular imaging, e.g., IVUS, OCT, etc., and one (1) view of angiography. In the description below, while intravascular imaging of the present disclosure is not limited to OCT, OCT is used as a representative of intravascular imaging for describing one or more features herein.

Figure 1B:
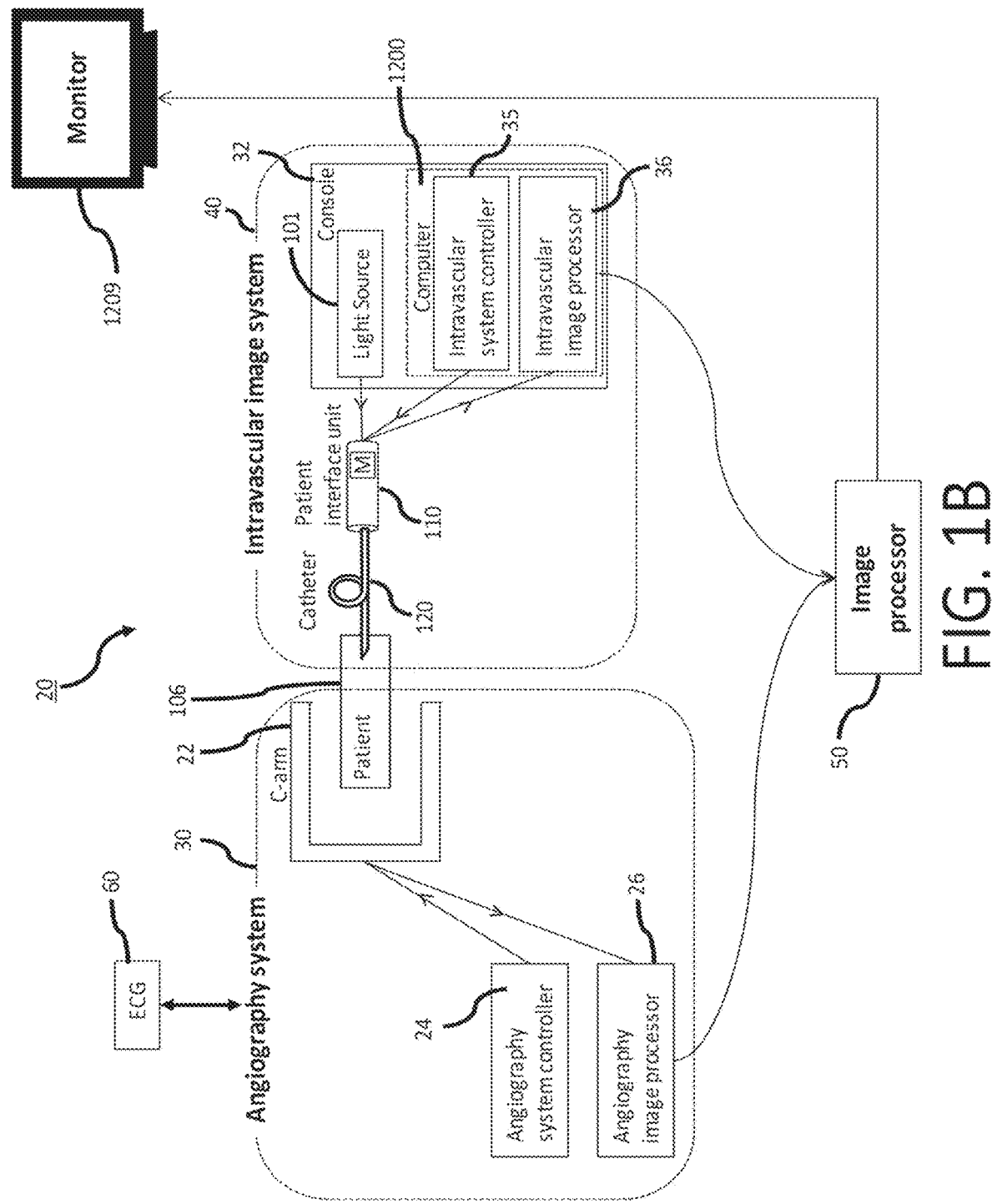
FIG. 1B is a schematic diagram illustrating an imaging system for executing one or more steps to process image data in accordance with one or more aspects of the present disclosure.

Referring now to FIG. 1B, shown is a schematic diagram of at least one embodiment of an imaging system 20 for generating an imaging catheter path based on either a directly detected location of a radiopaque marker on the imaging catheter or a regression line representing the imaging catheter path by using an angiography image frame that is simultaneously acquired during intravascular imaging pullback. The imaging system 20 may include an angiography system 30, an intravascular imaging system 40, an image processor 50, a display or monitor 1209, and an electrocardiography (ECG) device 60. The angiography system 30 includes an X-ray imaging device such as a C-arm 22 that is connected to an angiography system controller 24 and an angiography image processor 26 for acquiring angiography image frames of an object or patient 106.

The intravascular imaging system 40 of the imaging system 20 may include a console 32, a catheter 120 and a patient interface unit or PIU no that connects between the catheter 120 and the console 32 for acquiring intravascular image frames. The catheter 120 may be inserted into a blood vessel of the patient 106. The catheter 120 may function as a light irradiator and a data collection probe that is disposed in the lumen of a particular blood vessel, such as, for example, a coronary artery. The catheter 120 may include a probe tip, one or more radiopaque markers, an optical fiber, and a torque wire. The probe tip may include one or more data collection systems. The catheter 120 may be threaded in an artery of the patient 106 to obtain images of the coronary artery. The patient interface unit no may include a motor M inside to enable pullback of imaging optics during the acquisition of intravascular image frames. The imaging pullback procedure may obtain images of the blood vessel. The imaging pullback path may represent the co-registration path, which may be a region of interest or a targeted region of the vessel.

The console 32 may include a light source(s) 101 and a computer 1200. The computer 1200 may include features as discussed herein and below (see e.g., FIG. 11), or alternatively may be a computer 1200' (see e.g., FIG. 12) or any other computer or processor discussed herein. In one or more embodiments, the computer 1200 may include an intravascular system controller 35 and an intravascular image processor 36. The intravascular system controller 35 and/or the intravascular image processor 36 may operate to control the motor M in the patient interface unit 110. The intravascular image processor 36 may also perform various steps for image processing and control the information to be displayed.

Various types of intravascular imaging systems may be used within the imaging system 20. The intravascular imaging system 40 is merely one example of an intravascular imaging system that may be used within the imaging system 20. Various types of intravascular imaging systems may be used, including, but not limited to, an OCT system, a multi-modality OCT system or an IVUS system, by way of example.

The imaging system 20 may also connect to an electrocardiography (ECG) device 60 for recording the electrical activity of the heart over a period of time using electrodes placed on the skin of the patient 106. The imaging system 20 may also include an image processor 40 for receiving angiography data, intravascular imaging data, and data from the ECG device 6o to execute various image-processing steps to transmit to a display 1209 for displaying an angiography image frame with a co-registration path. Although the image processor 40 associated with the imaging system 20 appears external to both the angiography system 20 and the intravascular imaging system 30 in FIG. 1B, the image processor 40 may be included within the angiography system 30, the intravascular imaging system 40, the display 1209 or a stand-alone device. Alternatively, the image processor 40 may not be required if the various image processing steps are executed using one or more of the angiography image processor 26, the intravascular image processor 36 of the imaging system 20, or any other processor discussed herein (e.g., computer 1200, computer 1200', computer or processor 2, etc.).

Figure 2:
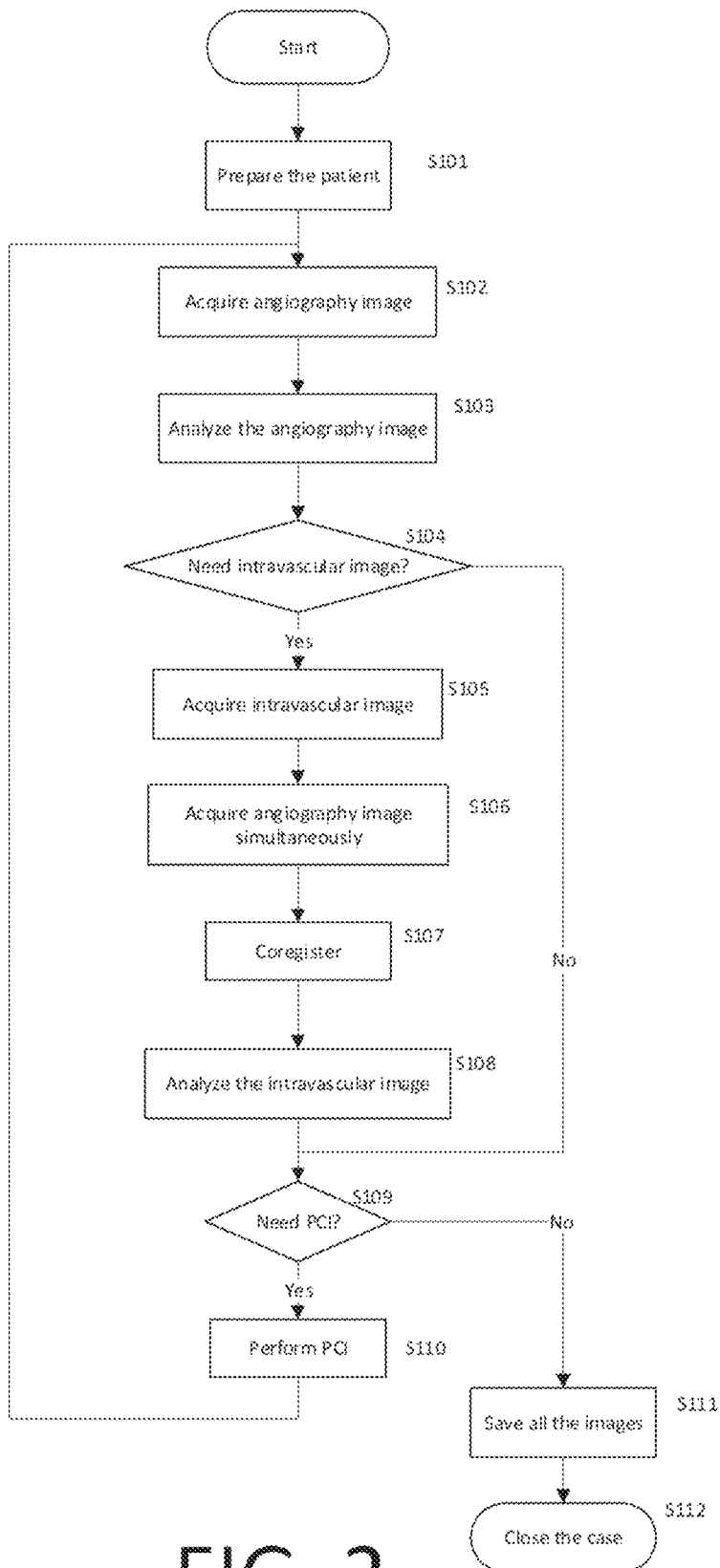
FIG. 2 is a flowchart of at least one embodiment of an interventional procedure that may be used in accordance with one or more aspects of the present disclosure.

FIG. 2 shows at least one embodiment of workflow or overall workflow in a catheterization lab (also discussed herein as "cath lab"). In one or more embodiments, construction or reconstruction of the 3D structure (e.g., a 3D vessel) may be performed after step S107 shown in FIG. 2 and as discussed further below.

Figure 3:
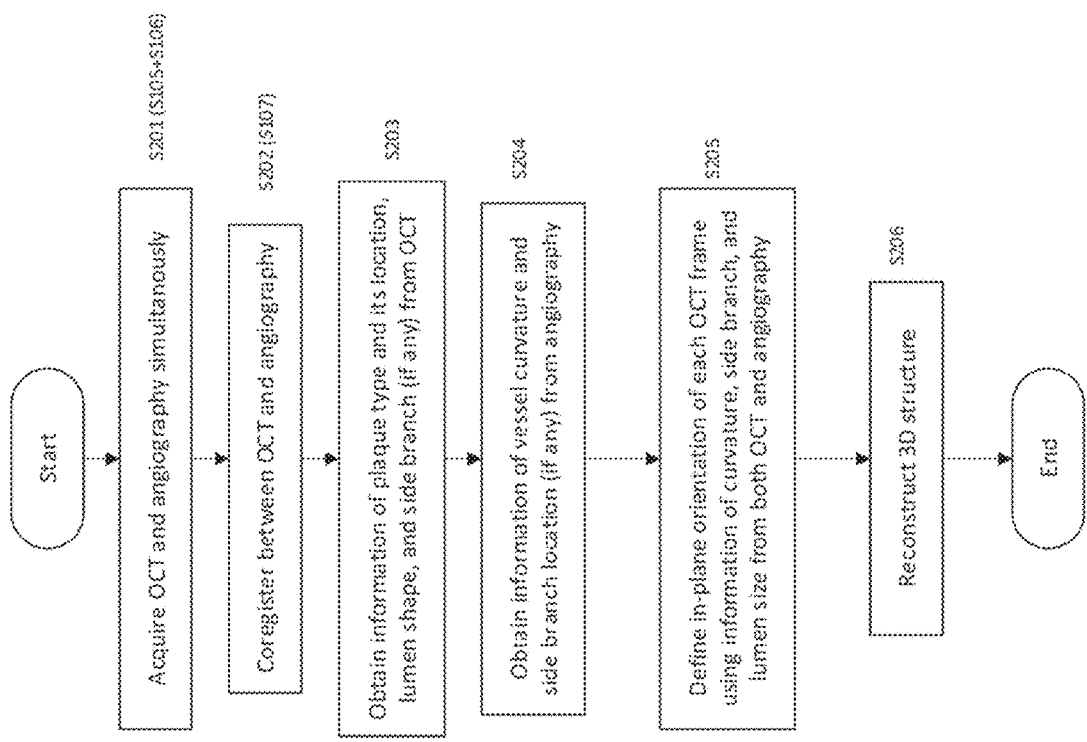
FIG. 3 is a flowchart of at least one embodiment of a method for performing a 3D construction or reconstruction from OCT and one (1) view of angiography that may be used in accordance with one or more aspects of the present disclosure.

FIG. 3 shows at least one embodiment of workflow of 3D construction or reconstruction from intravascular imaging (e.g., OCT as shown in FIG. 3) and one (1) view of angiography.

Embodiments of overall workflow in a cath lab and embodiments of construction or reconstruction of 3D structure(s) may be used in combination. While not limited to the discussed combination or arrangement, one or more steps may be involved in both of the workflows or processes in one or more embodiments of the present disclosure, for example, as shown in FIG. 2 and/or FIG. 3 and as discussed below.

Returning to the details of FIG. 2, one or more methods or processes of the present disclosure may include one or more of the following steps: (i) preparing the patient (see step S101 in FIG. 2); (ii) acquiring an angiography image (see step S102 in FIG. 2); (iii) analyzing the angiography image (see step S103 in FIG. 2); (iv) determining whether an intravascular image is needed (see step S104 in FIG. 2); (v) in a case where "Yes" is the result in step S104, acquiring the intravascular image (see step S105 in FIG. 2), acquiring an angiography image (e.g., simultaneously such that steps S105 and S106 may be performed to simultaneously acquire the intravascular (e.g., OCT) image and the angiography image, at a different time than the intravascular image is acquired, etc.) (see step S106 in FIG. 2), performing co-registration (see step S107 in FIG. 2), analyzing the intravascular image (see step S108 in FIG. 2), and then proceeding to step S109, or in a case where "No" is the result in step S104, proceeding to step S109 (and skipping or bypassing steps S105-S108 as shown in FIG. 2); (vi) determining whether PCI is needed or not (see step S109 in FIG. 2); (vii) in a case where "Yes" is the result in step S109, performing PCI (see step S110 in FIG. 2) and then returning to step S102 as shown in FIG. 2, or in a case where "No" is the result in step S109, saving all the images (see step S111 in FIG. 2) and then closing the case (see step S112) to end the process. It is understood that simultaneous acquisition of, for example, an angiographic image and an OCT intravascular image may be performed at a different amount of time (e.g., milliseconds compared to several seconds). Thus, the term 'simultaneous' include an angiographic image (or multiple angiographic images) taken at any time during an OCT pullback. While steps S105 and S106 may be performed to simultaneously acquire the intravascular image and the angiography image in one or more embodiments, such image acquisition may be performed at different times (or not being simultaneously acquired) in one or more other embodiments, such as, but not limited to, embodiment(s) as discussed in U.S. Pat. App. No. 62/798,885, filed on Jan. 30, 2019, the application of which is incorporated by reference herein in its entirety. Indeed, co-registration may be performed under either scenario. In one or more embodiments where an angiography image is acquired simultaneously with an intravascular image, the one or more such embodiments may increase the accuracy of the co-registration because a radiopaque marker location, which is the acquisition location of an intravascular (e.g., OCT) image, may be detected. In one or more embodiments, OCT/IVUS and angiography modalities are available when using images that are acquired during a procedure (e.g., a PCI procedure). In one or more embodiments, where a CT image is acquired prior to the PCI procedure, co-registration between CT and angiography, and/or between CT and OCT/IVUS, may be performed. Using CT and OCT/IVUS is further discussed in U.S. Pat. Pub. No. 2018/0271614, which publication is incorporated by reference herein in its entirety. While one or more PCI procedures discussed herein discusses stent implantation, balloon angioplasty or other procedures in coronary arteries and other arteries (e.g., arteries located in one or more legs or other body parts), PCT procedures are not limited thereto. For example, in addition to uses for coronary procedures, OCT/IVUS may be used in other region(s) of vasculature. In one or more embodiments, the angiography image(s) obtained in step S102 may be used for an initial analysis of a patent or the case, and the second angiography image(s) obtained in step S105 may be used for co-registration. The second angiography image(s) obtained in step S105 may be obtained during OCT pullback to achieve more accurate co-registration.

While not limited to this process, construction or reconstruction of a 3D structure(s) (e.g., of a 3D vessel) may be performed, for example, as shown in FIG. 3. For example, at least one embodiment may include one or more of the following steps: (i) acquiring OCT and angiography image(s), for example, simultaneously, at different times or not simultaneously, etc. (see step S201 in FIG. 3 and steps S105 and S106 in FIG. 2); (ii) performing co-registration between OCT and angiography (see step S202 in FIG. 3; e.g., at least one example co-registration method may be detecting a radiopaque marker that is on the OCT catheter in each angiography image frame); (iii) analyzing the OCT image to obtain information of a plaque type and its location, of a lumen shape and/or size, and of side branch or branches (if any) (see step S203 in FIG. 3); (iv) using the angiography image to analyze object (e.g., a vessel) curvature and size branch location(s) (if any) (see step S204 in FIG. 3); (v) after obtaining information from both the OCT image and the angiography image, determining an acquisition location of the intravascular image in the object (or the object to be examined), that is visualized in the angiography image, and/or defining or determining an in-plane orientation of the intravascular image based on the intravascular image and the angiography image or an in-plane orientation of each OCT frame (e.g., rotational orientation of an OCT frame in the plane that is vertical to a co-registration path and/or a longitudinal direction of the object (e.g., the vessel)) based on the information from both the OCT and angiography images (see step S205 in FIG. 3); and (vi) constructing or reconstructing the 3D structure(s) (e.g., a 3D vessel, a 3D object, etc.) (see step S206 in FIG. 3). In one or more embodiments, the order of steps S203 and S204 may be switched or may occur contemporaneously or simultaneously. For example, in one or more embodiments, an order may be flipped between step S202 and steps S203-S204, e.g., step S201 may proceed to step S203 and step S204. Step S202 may be performed after steps S203-S204, and then, after completion of step S202, the process may proceed to step S205 and step S206.

Figure 4:
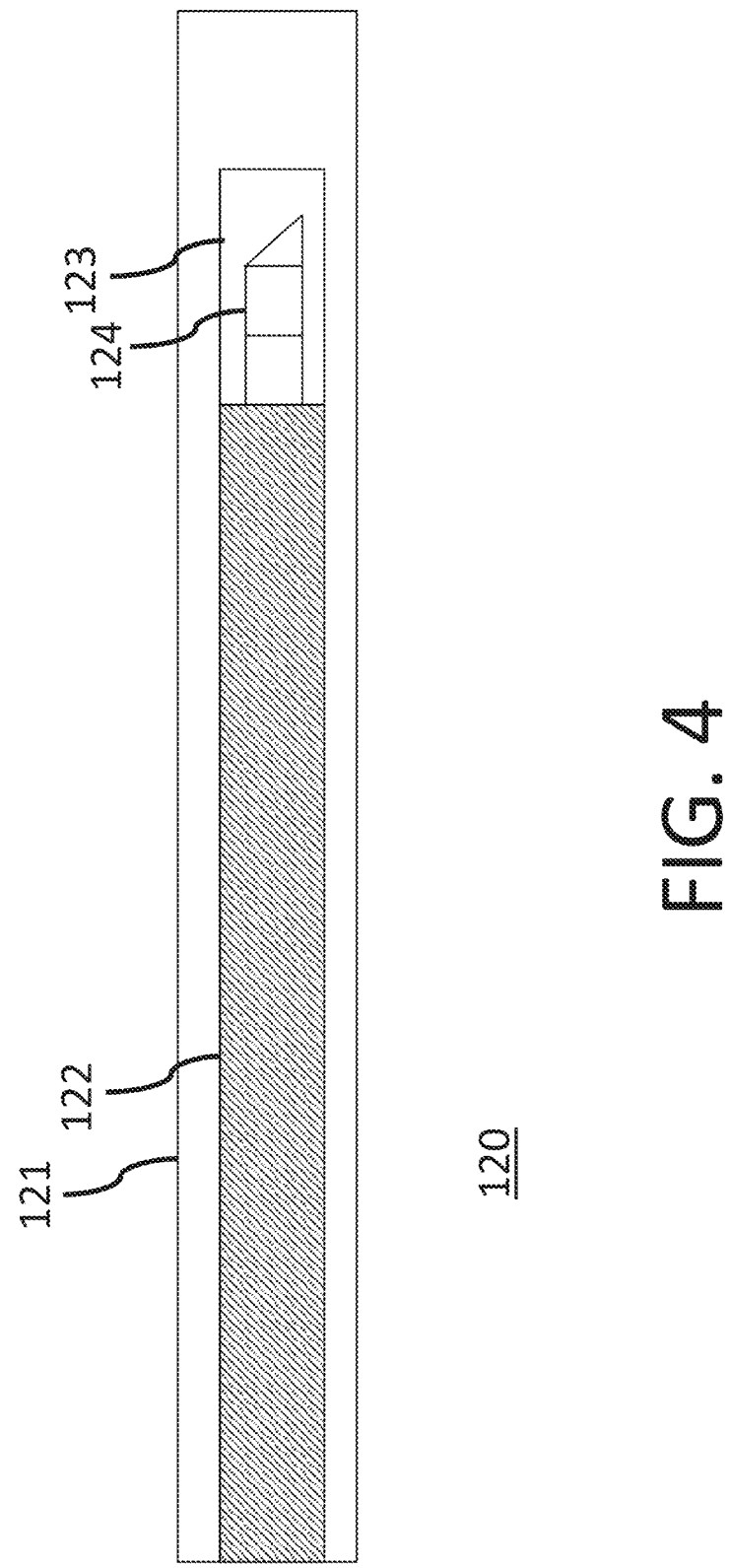
FIG. 4 is a diagram of at least one embodiment of a catheter that may be used with one or more embodiments for constructing or reconstructing 3D structure(s) in accordance with one or more aspects of the present disclosure.

FIG. 4 shows at least one embodiment of a catheter 120 that may be used in one or more embodiments of the present disclosure to obtain images and/or to construct or reconstruct 3D structure(s). FIG. 4 shows an embodiment of the catheter 120 including a sheath 121, a coil 122, a protector 123 and an optical probe 124. As shown schematically in FIGS. 9A-9C (discussed further below), the catheter 120 may be connected to a patient interface unit (PIU) 110 to spin the coil 122 with pullback (e.g., at least one embodiment of the PIU 110 operates to spin the coil 122 with pullback). The coil 122 delivers torque from a proximal end to a distal end thereof (e.g., via or by a rotational motor in the PIU 110). In one or more embodiments, the coil 122 is fixed with/to the optical probe 124 so that a distal tip of the optical probe 124 also spins to see an omnidirectional view of the object (e.g., a biological organ, sample or material being evaluated, such as, but not limited to, hollow organs such as vessels, a heart, a coronary artery, etc.). For example, fiber optic catheters and endoscopes may reside in the sample arm (such as the sample arm 103 as shown in one or more of FIGS. 9A-9C discussed below) of an OCT interferometer in order to provide access to internal organs, such as intravascular images, gastro-intestinal tract or any other narrow area, that are difficult to access. As the beam of light through the optical probe 124 inside of the catheter 120 or endoscope is rotated across the surface of interest, cross-sectional images of one or more objects are obtained. In order to acquire three-dimensional data, the optical probe 124 is simultaneously translated longitudinally during the rotational spin resulting in a helical scanning pattern. This translation is most commonly performed by pulling the tip of the probe 124 back towards the proximal end and therefore referred to as a pullback.

The catheter 120, which, in one or more embodiments, comprises the sheath 121, the coil 122, the protector 123 and the optical probe 124 as aforementioned (and as shown in FIG. 4), may be connected to the PIU 110. In one or more embodiments, the optical probe 124 may comprise an optical fiber connector, an optical fiber and a distal lens. The optical fiber connector may be used to engage with the PIU 110. The optical fiber may operate to deliver light to the distal lens. The distal lens may operate to shape the optical beam and to illuminate light to the object (e.g., the object 106 (e.g., a vessel) discussed herein), and to collect light from the sample (e.g., the object 106 (e.g., a vessel) discussed herein) efficiently.

As aforementioned, in one or more embodiments, the coil 122 delivers torque from a proximal end to a distal end thereof (e.g., via or by a rotational motor in the PIU 110). There may be a mirror at the distal end so that the light beam is deflected outward. In one or more embodiments, the coil 122 is fixed with/to the optical probe 124 so that a distal tip of the optical probe 124 also spins to see an omnidirectional view of an object (e.g., a biological organ, sample or material being evaluated, such as, but not limited to, hollow organs such as vessels, a heart, a coronary artery, etc.). In one or more embodiments, the optical probe 124 may include a fiber connector at a proximal end, a double clad fiber and a lens at distal end. The fiber connector operates to be connected with the PIU 110. The double clad fiber may operate to transmit & collect OCT light through the core and, in one or more embodiments, to collect Raman and/or fluorescence from an object (e.g., the object 106 (e.g., a vessel) discussed herein, an object and/or a patient (e.g., a vessel in the patient), etc.) through the clad. The lens may be used for focusing and collecting light to and/or from the object (e.g., the object 106 (e.g., a vessel) discussed herein). In one or more embodiments, the scattered light through the clad is relatively higher than that through the core because the size of the core is much smaller than the size of the clad.

Figure 5:
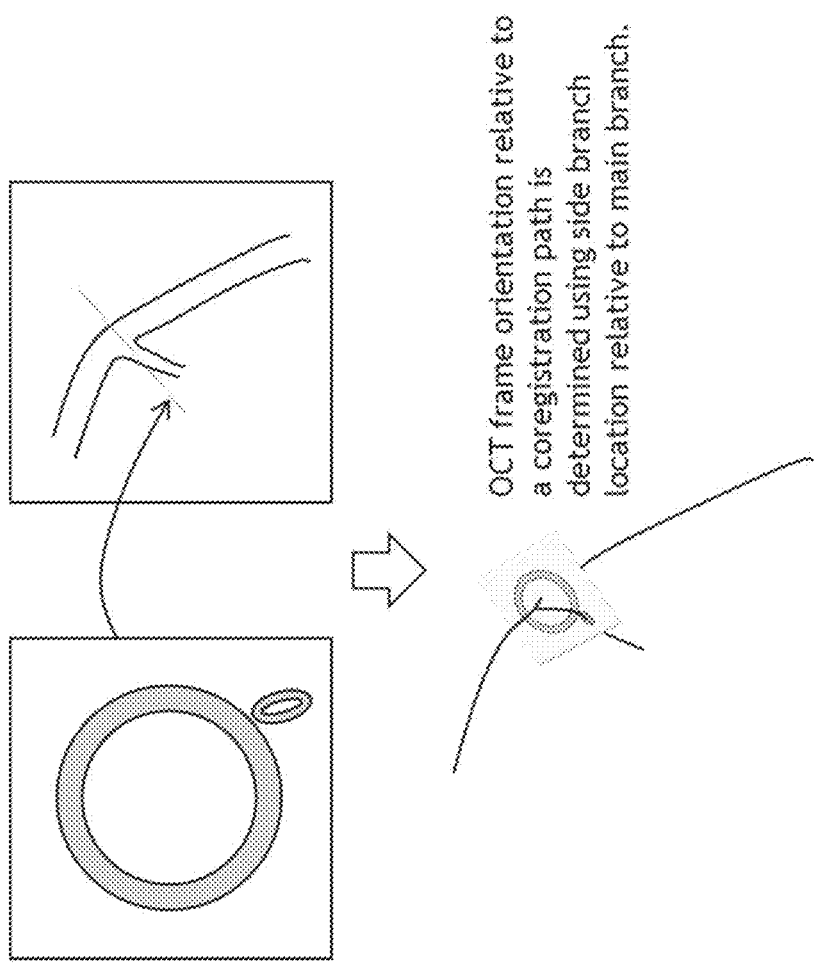
FIG. 5 is a diagram of at least one embodiment that may use side branch information to determine in-plane orientation in accordance with one or more aspects of the present disclosure.

While construction or reconstruction of a 3D structure(s) may be performed with or without side branch information, FIG. 5 describes one of the methods of the present disclosure that uses side branch information. For example, OCT frame orientation relative to a co-registration (or coregistration) path may be determined using side branch location(s) relative to a main branch of the object (e.g., the vessel, the object to be imaged or examined, etc.). In one or more embodiments, in a case where a lumen shape (e.g., of the object (e.g., the vessel)) is oval, the diameter of the lumen may be used to decide the in-plane orientation by matching the diameter of the lumen between OCT and angiography image(s). In addition to determining in-plane orientation, the side branch location(s) may be used to correct the co-registration between OCT and angiography, if needed. Then, the structure of the object (e.g., the vessel) may be constructed or reconstructed in 3D space. Since coregistration between OCT and angiography may provide the acquisition location of each OCT frame on a vessel tree that is shown in the angiography image, each OCT frame may be placed perpendicularly to the coregistration path with the determined in-plane orientation. After that, lumen surface, plaque surface, and other structure(s) may be interpolated between each OCT frame. This interpolation may be done as straight lines or splines in one or more embodiments. In one or more embodiments, if multiple side branches are identified, OCT frame in-plane orientation may be determined based on one of the side branches and may be updated or modified using other side branches. The side branch or branches that is/are used to define and/or determine in-plane orientation at first may be selected by a user or may be selected automatically by the processor or computer. Additionally or alternatively, all the side branches may be used to determine in-plane orientation at each location.

Figure 6A:
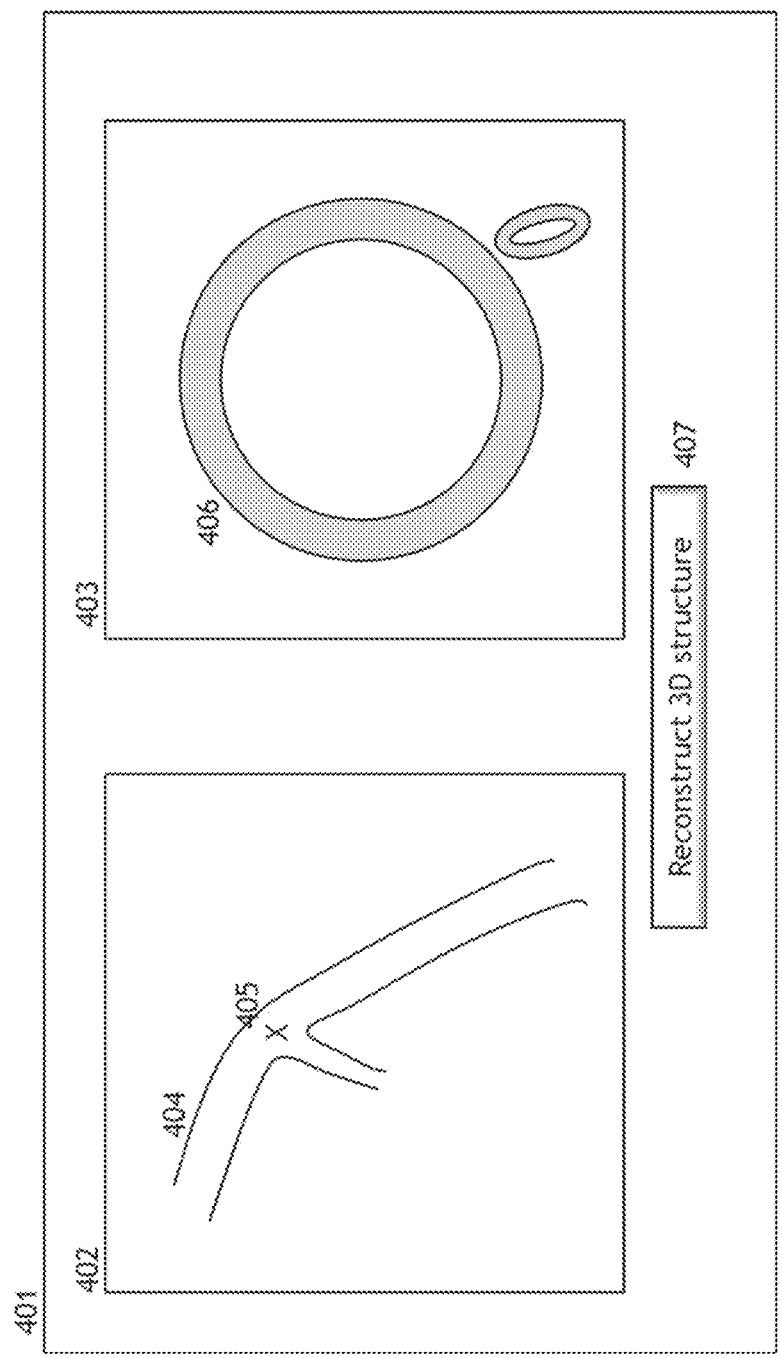
FIGS. 6A-8 are embodiment examples Graphical User Interfaces (GUIs) that may be used for determining in-plane orientation in accordance with one or more aspects of the present disclosure.
Figure 6B:
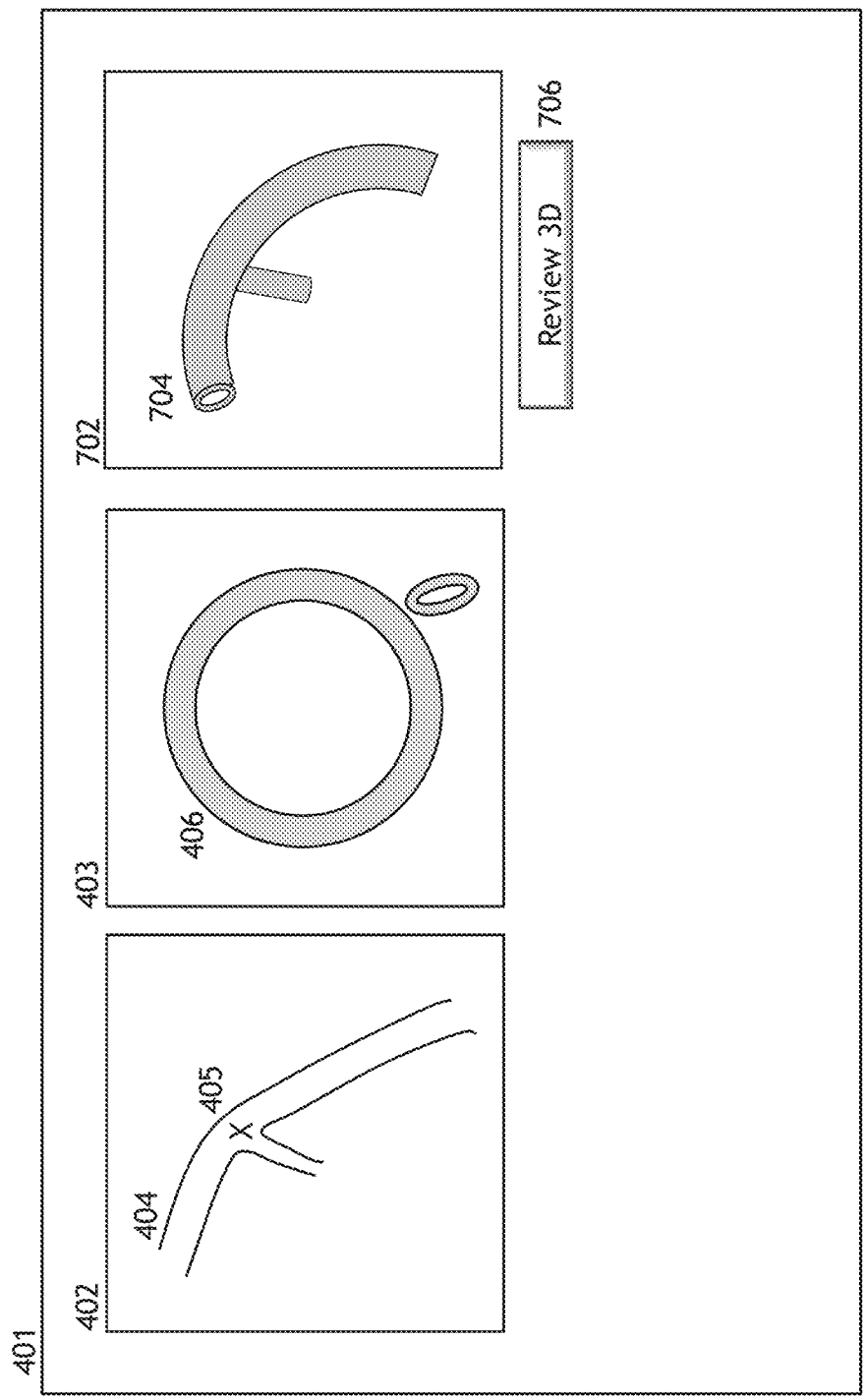
Figure 7:
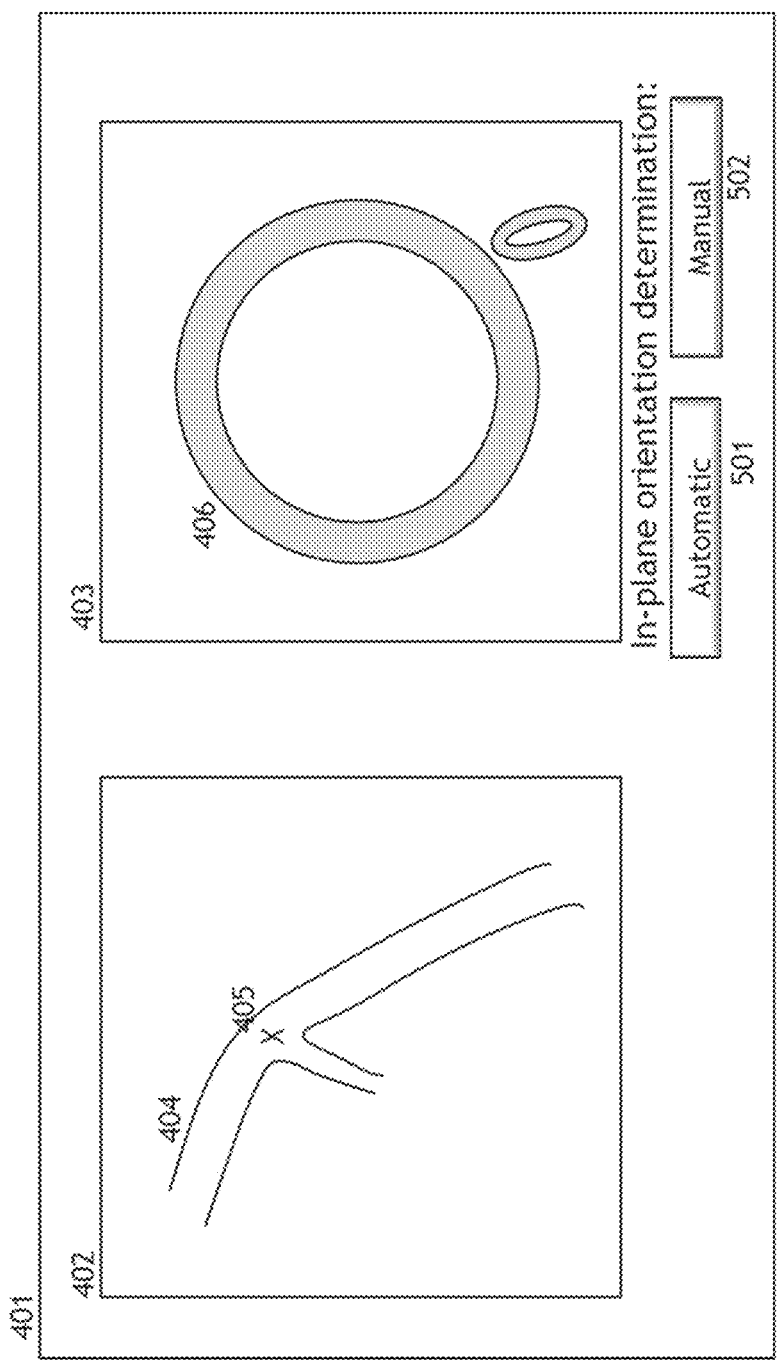
Figure 8:
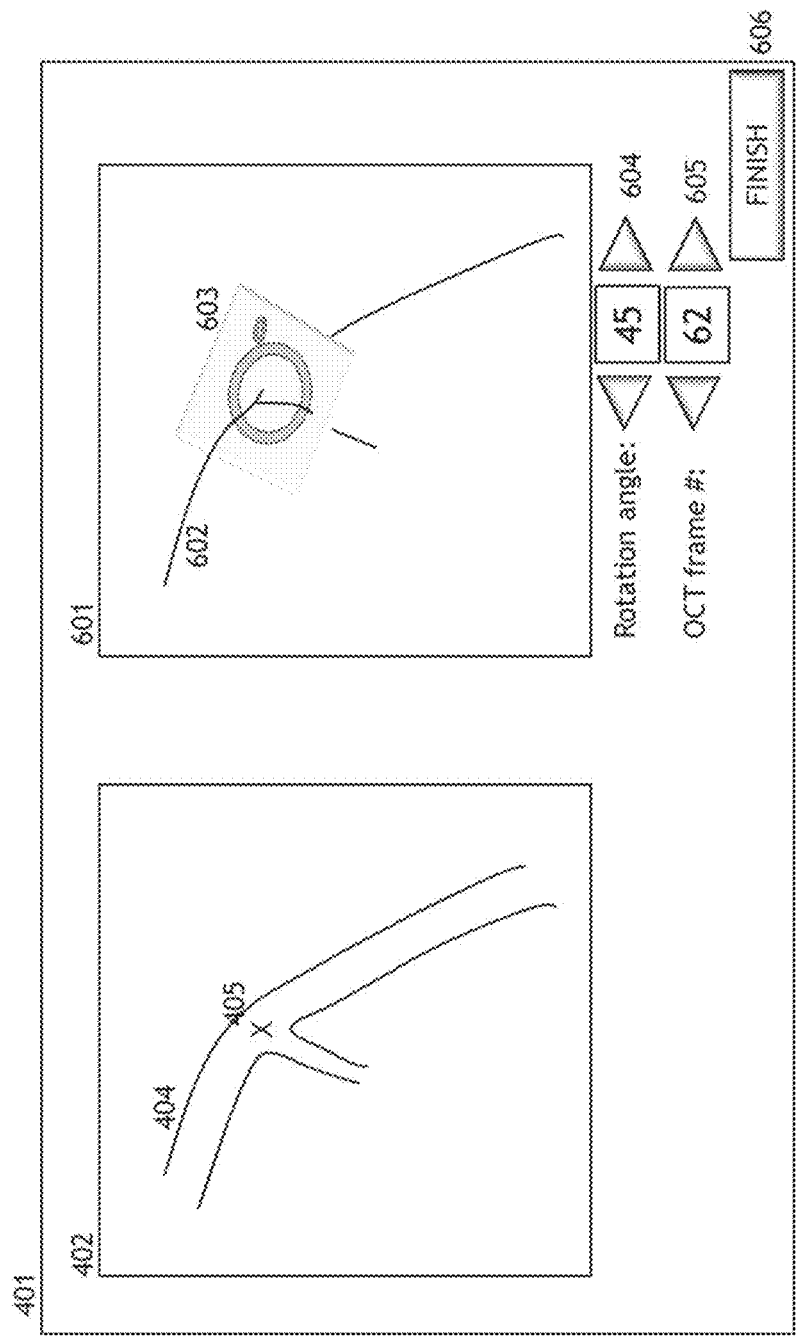

In one or more additional or alternative embodiments, a user (e.g., a physician, a clinician, etc.) may determine the in-plane orientation based on the user's preference. FIGS. 6-8 show example graphical user interfaces (GUIs) that may be used to allow the user to determine the in-plane orientation in one or more ways. For example, after step S202 in FIG. 3, the GUI screen 401 shown in FIG. 6A may be displayed to the user to initiate construction or reconstruction of a 3D structure(s) (e.g., of the vessel), for example, via a button 407 to initiate the 3D construction or reconstruction. The angiography view 402 may be displayed side by side with the OCT view 403. A vessel tree 404 in the angiography view 402 may be shown along with an acquisition location of the OCT frame that is shown in the OCT view 403. The OCT frame may display the cross-sectional view 406 of the vessel. The "Reconstruct 3D structure" (construction or reconstruction button) button 407 may be displayed anywhere in the GUI screen 401 (e.g., as shown in the bottom of the GUI screen 401 in FIG. 6A). After a 3D structure is constructed or reconstructed, the structure may be displayed on a GUI, and a user may review the data. FIG. 6B is an example GUI. In this example, constructed or reconstructed structure 704 is displayed 702 along with an angiography view 402 and an OCT view 403. The "Review 3D" button 706 may initiate detailed review of the constructed or reconstructed structure by a user, such as rotating the angle and zooming in to a specific location. This button may be displayed anywhere in the GUI screen 401. In one or more embodiments, this button may not be displayed if detailed review by a user is initiated directly by interacting with the constructed or reconstructed structure, such as via clicking on the structure 704. If a user prefers, a user may only see a 3D constructed or reconstructed structure or a 3D constructed or reconstructed structure with an angiography view 402 or OCT view 403 only.

In a case where the construction or reconstruction process is initiated (e.g., by selecting the button 407 in FIG. 6A), the user may be asked (via an updated GUI screen 401 shown in FIG. 7) whether the user prefers to specify or determine the in-plane orientation (e.g., automatically or manually). As shown in FIG. 7, the user may select the "Automatic" button 501 if an automatic in-plane orientation determination is preferred, or the user may select the "Manual" button 502 if a manual in-plane orientation determination is preferred. In a case where a user chooses the "Automatic" button 501, one or more of the process(es) described above and shown in FIGS. 2-3 and 5-7 may be performed. In a case where a user chooses the "Manual" button 502, one or more GUIs, for example, the GUI 401 of FIG. 8, may be shown to a user. In the GUI of FIG. 8, the OCT frame 603 is shown as being placed on the coregistration path 602 with the specified rotation angle on the plane (e.g., as specified via the box or triangle rotation angle input fields or buttons 604) in the OCT view to determine in-plane orientation 601. A user may modify the rotation angle by typing a number in the box and/or clicking the triangles of the rotation angle input fields or buttons 604 (e.g., as shown in FIG. 8). A user may also modify the OCT frame number to specify the in-plane orientation for a predetermined or desired frame number by typing the frame number in the box and/or clicking triangles of the OCT frame number input fields or buttons 605 (e.g., as shown in FIG. 8). Once a user finishes determining in-plane orientation for a desired or predetermined number of OCT frames or all the OCT frames, a user may press a "FINISH" button 606 (e.g., as shown in FIG. 8). Additionally or alternatively, if a user prefers, a user may modify the result of automatic determination of in-plane orientation using a similar GUI of FIG. 8 after one or more of the processes discussed above and/or as shown in FIGS. 2-3 and FIGS. 5-7 is performed to obtain the automatic determination.

In one or more embodiments, if a user prefers or desires, before initiating a 3D construction or reconstruction process or during a 3D construction or reconstruction process, the co-registration location may be modified. As an example, in the GUI of FIG. 8, a user may drag a marker 405 to a desired location. If a marker, such as the marker 405, is moved, the location of the OCT frame on the coregistration path 603 may be moved to reflect the modification.

After constructing or reconstructing the 3D structure of the vessel, a user may use the constructed or reconstructed 3D structure to assess physiological information at the object, or predetermined location in the object (e.g., at a lesion). Since a blood flow rate may be different between an inside and an outside of a curvature, having a curvature information in the 3D structure may provide a more accurate CFD result (e.g., a CFD model for the object or a predetermined location in the object). In addition, since the existence of a side branch (or branches) and the location of the side branch (or branches) relative to the curvature changes the flow pattern and flow rate, as well as the precise information of lumen size, having that information in the 3D structure may add or provide more accuracy in the CFD result or model.

The constructed or reconstructed result of the 3D structure of the object, or the predetermined location in the object (e.g., the vessel) may be used just for visualization in one or more embodiments. Including vascular curvature information in a construction or reconstruction (e.g., a volumetric construction or reconstruction) from OCT that may be visualized in a GUI provides useful information to the user (e.g., the physician, the clinician, etc.). By having both curvature information and side branch information in one or more embodiments, such information helps a user to plan the location of implants, such as, but not limited to, a stent, other interventional device, etc., to reduce or minimize the influence on the side branch and/or to reduce or minimize a risk of implant rupture (e.g., stent rupture).

Visualization, PCI procedure planning, and physiological assessment may be combined to perform complete PCI planning beforehand, and to perform complete assessment after the procedure. Once a 3D structure is constructed or reconstructed and a user specifies an interventional device, e.g., a stent, that is planned to be used, virtual PCI may be performed in a computer simulation (e.g., by one or more of the computers discussed herein, such as, but not limited to, the computer 2, the processor computer 1200, the processor or computer 1200', any other processor discussed herein, etc.). Then, another physiological assessment may be performed based on the result of the virtual PCI. This approach allows a user to find the best device (e.g., interventional device, implant, stent, etc.) for each patient before or during the procedure.

In one or more additional or alternative embodiments, one or more other imaging modalities may be used, such as CT and/or magnetic resonance imaging (MRI), to define a curvature of an object (e.g., a vessel) instead of using an angiography image. Since multiple slices may be captured with CT or MRI, a 3D structure of the object (e.g., a vessel) may be reconstructed from CT. Intravascular imaging may add the information of plaque type and its location, and potentially provide more accurate lumen size and shape information for the 3D structure.

While a few examples of GUIs have been discussed herein and shown in one or more of the figures of the present disclosure, other GUI features, imaging modality features, or other imaging features, may be used in one or more embodiments of the present disclosure, such as the GUI feature(s), imaging feature(s), and/or imaging modality feature(s) disclosed in U.S. patent Ser. No. 16/401,390, filed May 2, 2019, which was published as U.S. Pat. Pub. No. 2019/0339850 on Nov. 7, 2019, and disclosed in U.S. Pat. Pub. No. 2019/0029624 and WO 2019/023375, which application(s) and publication(s) are incorporated by reference herein in their entireties.

One or more methods or algorithms for calculating stent expansion/underexpansion or apposition/malapposition may be used in one or more embodiments of the present disclosure, including, but not limited to, the expansion/underexpansion and apposition/malapposition methods or algorithms discussed in U.S. Pat. Pub. Nos. 2019/0102906 and 2019/0099080, which publications are incorporated by reference herein in their entireties.

One or more methods or algorithms for calculating or evaluating cardiac motion using an angiography image and/or for displaying anatomical imaging may be used in one or more embodiments of the present disclosure, including, but not limited to, the methods or algorithms discussed in U.S. Pat. Pub. No. 2019/0029623 and U.S. Pat. Pub. No. 2018/0271614 and WO 2019/023382, which publications are incorporated by reference herein in their entireties.

One or more methods or algorithms for performing co-registration and/or imaging may be used in one or more embodiments of the present disclosure, including, but not limited to, the methods or algorithms discussed in U.S. Pat. App. No. 62/798,885, filed on Jan. 30, 2019 and published as WO 2020/159984, and discussed in U.S. Pat. Pub. No.

2019/0029624, which application(s) and publication(s) are incorporated by reference herein in their entireties.

For example, other options may be included in the GUI, such as, but not limited to, a Mark Slice feature, a Snapshot feature, an Annotation feature, etc. The Snapshot feature operates to take a snapshot or image of the current view of the GUI. The Annotation feature operates to allow a user of the GUI to include a comment(s) or note(s) for the viewed image or images. The Mark Slice feature allows the user to set points in a pullback feed of slices that are of interest (i.e., to mark a desired slice or slices).

Another option, in one or more embodiments, is a setting or feature icon or drop down menu that allows a user of the GUI to calculate one or more details of the image(s), such as, but not limited to, expansion/underexpansion (e.g., related to a reference area, of a stent, etc.), malapposition (e.g., of a stent, of a medical implant, etc.), etc. Information may be displayed to the right of the menu, such as, but not limited to, a percentage value of the reference area (e.g., "0-80% reference area" which indicates underexpansion exists in one or more embodiments and ma may be associated with a red box (or a box of a predetermined color) near or to the left of that information; "80-90% reference area" which may indicate that an issue may or may not exist (e.g., the underexpansion may fall within an acceptable range) related to underexpansion and may be associated with a yellow box (or a box of a predetermined color) near or to the left of that information, "90-100% reference area" which may indicate that an issue may not exist related to underexpansion and may be associated with a green box (or a box of a predetermined color) near or to the left of that information; etc.). Any colored box may be set at a predetermined location as desired in one or more embodiments. Such information and indicators may be used for apposition/malapposition in one or more embodiments. Additionally or alternatively, apposition/malapposition may be indicated with different predetermined ranges, such as, but not limited to, for example, greater than 300 microns (in other words, 300 microns or greater) may be used as the range for the red region or a region that needs or may need correction or action (e.g., a high risk region); between 200-300 microns may be used for the yellow region or a region that may need correction or action or to be watched closely or a region that is in an acceptable range to take no action or make no correction (e.g., a region between high and low risk, an acceptable region, etc.); less than 200 microns may be used for the green region or a region that has no issue detected and/or may require no action (e.g., a low risk region); etc. In one or more embodiments, different values or ranges may be assigned to the limits or ranges for the red or high risk region, the yellow or middle region and/or the green or acceptable region, for instance. The subject ranges may be decided by the apparatus, GUI, system, method, or storage medium automatically or may be selected by a user (e.g., a physician) manually. Depending on the application and use of the one or more embodiments of the present disclosure, such values may change accordingly. Other ranges may be designated for the high/low risk and/or acceptable or attention needed regions depending on the needs of a user and the medical procedure to be performed. Based on the data and associated warning or information displayed related to expansion/underexpansion and/or the apposition/malapposition, the GUI operates to indicate to a user of the GUI how to respond to that information (e.g., expansion/underexpansion and/or apposition/malapposition falls within an acceptable range such that no action may be needed; expansion/underexpansion and/or apposition/malapposition falls outside of an acceptable range such that action may be needed; expansion/underexpansion and/or apposition/malapposition falls in a range that requires correction or correction may be suggested; etc.). Any of the subject ranges (or any other range or ranges discussed in the present disclosure) may be selected manually or automatically as aforementioned. Such examples allow a user of the GUI to identify potential issues identified by the data in the one or more images, and may make appropriate decisions and create a plan accordingly.

Such information and other features discussed herein may be applied to other applications, such as, but not limited to, co-registration, other modalities, etc. Indeed, the useful applications of the features of the present disclosure and of the aforementioned applications and patent publications are not limited to the discussed modalities, images, or medical procedures. Additionally, depending on the involved modalities, images, or medical procedures, one or more control bars may be contoured, curved, or have any other configuration desired or set by a user. For example, in an embodiment using a touch screen as discussed herein, a user may define or create the size and shape of a control bar based on a user moving a pointer, a finger, a stylus, another tool, etc. on the touch screen (or alternatively by moving a mouse or other input tool or device regardless of whether a touch screen is used or not).

As aforementioned, one or more methods or algorithms for calculating expansion/underexpansion or apposition/malapposition may be used in one or more embodiments of the instant application, including, but not limited to, the expansion/underexpansion and apposition/malapposition methods or algorithms discussed in U.S. Pat. Pub. Nos. 2019/0102906 and 2019/0099080, which publications are incorporated by reference herein in their entireties. For example, in one or more embodiments for evaluating expansion/underexpansion, a method may be performed to remove inappropriate OCT image frames from the OCT image from further image processing. The result of lumen detection may be checked for each OCT image frame. If the lumen is not detected or if the detected lumen is affected by any artifact, the OCT image frame may be removed. A first OCT image frame is selected from the OCT image in a first step. After selecting the first OCT image frame, it may be determined whether a lumen is detected in the selected OCT image frame. If it is determined that no lumen has been detected in the OCT image frame, then the OCT image frame may be removed from further image processing and the process continues. Alternatively, if the lumen is detected in the frame, then a further determination of whether the detected lumen is affected by any artifact may be performed. If the detected lumen is affected by an artifact, then the OCT image frame may be removed from further processing and the process proceeds. If the detected lumen is not affected by any artifact, then it may be determined if the selected OCT image frame is the last OCT image frame from the OCT image. If the selected frame is not the last frame in the OCT image, then the next OCT image frame from the OCT image may be selected and the process returns to the lumen detection on the frame step. If the selected OCT image frame is the last OCT image frame, then the process proceeds. After removing the inappropriate OCT image frames, all the OCT image frames in which stent-struts are detected may be selected (Group $G_S'$). It may that the entire range of the stent region in the OCT image is going to be evaluated for stent expansion in one or more embodiments, but in another embodiment in this step a user may select one or more (first) ranges for evaluating stent expansion, from the stent region where the stent is implanted and the stent-struts are detected. Whether the user selects the first range as the entire range of the stent region or as a partial range of the entire stent region may depend upon system requirements or user needs. In one embodiment, the user may use a mouse device or touch screen device to designate one or more (first) ranges in the stent region, and a processor or CPU (e.g., the computer or processor 1200, 1200', 2, etc. and/or any other processor discussed herein) may determine the first range for the stent expansion evaluation. This allows for designation of one or more positions. Subsequently, a reference OCT image frame based on the confirmed stented region may be selected. If the calculated stent length is equal to or within a predetermined threshold to the actual stent length, the OCT image frame at a position representing the distal end and the OCT image frame at a position representing the proximal end of the stented segment may be selected as reference frames. If the calculated stent length is not equal to the actual stent length and not within a predetermined threshold, the reference frames may be selected based on either the calculated stent length or the actual stent length. When the calculated stent length is selected for reference frame selection, the OCT image frame at a position representing the distal end and the OCT image frame at a position representing the proximal end of the stented segment may be selected as reference frames. Then, a reference OCT image frame may be selected based on the confirmed stented region. The reference area in the selected reference frame may be evaluated. Then, the first OCT image frame from the OCT image frames in which stent-struts are detected may be selected. Then the stent area is measured for the first OCT image frame. After measuring the stent area of the first OCT image frame, stent expansion may be evaluated by comparing the measured stent area and the reference area. The stent expansion value and an indicator for the corresponding stent expansion level may be saved with the first OCT image frame. After the stent expansion value is saved, it is determined whether the selected OCT image frame is the last frame. If the selected OCT image frame is not the last frame, then the next OCT image frame is selected and the process returns to the aforementioned measuring stent area step. In this example, because the selected OCT image frame is the first OCT image frame, the next frame would be the second OCT image frame from the group of all the OCT image frames in which stent-struts were detected. After selecting the next OCT image frame the process returns to the measure stent area step to measure the stent area for the next OCT image frame. Alternatively, if it is determined that the selected OCT image frame is the last frame, then the process for evaluating stent expansion is completed for the acquired OCT image. According to this workflow, every OCT image frame in which stent-struts are detected and not affected by artifact may be processed to obtain a stent expansion value based on the stent area associated with a selected OCT image frame and a reference area. In one or more embodiments, the reference area remains the same for each OCT image frame from the OCT image frames in which stent-struts are detected and not affected by artifact. By way of another example, in one or more embodiments for evaluating apposition/malapposition, a method may be performed to remove inappropriate OCT images as aforementioned. The result of lumen detection may be checked for each OCT image frame. If the lumen is not detected or if the detected lumen is affected by any artifact, the OCT image frame may be removed. A first OCT image frame is selected from the OCT image in a first step. After selecting the first OCT image frame, it may be determined whether a lumen is detected in the selected OCT image frame. If it is determined that no lumen has been detected in the OCT image frame, then the OCT image frame may be removed from further image processing and the process continues. Alternatively, if the lumen is detected in the frame, then a further determination of whether the detected lumen is affected by any artifact may be performed. If the detected lumen is affected by an artifact, then the OCT image frame may be removed from further processing and the process proceeds. If the detected lumen is not affected by any artifact, then it may be determined if the selected OCT image frame is the last OCT image frame from the OCT image. If the selected frame is not the last frame in the OCT image, then the next OCT image frame from the OCT image may be selected and the process returns to the lumen detection on the frame step. If the selected OCT image frame is the last OCT image frame, then the process proceeds. After removing the inappropriate OCT image frames, all the OCT image frames in which stent-struts are detected may be selected (Group $G_S'$). Then, a first OCT image frame from the selected OCT image frames in which stent-struts are detected may be selected. Subsequently, for the selected first OCT image frame, the distance between the lumen edge and stent-strut detected in first OCT image frame may be measured. Stent apposition may be evaluated. The stent apposition may be evaluated by comparing the measured distance between the lumen edge and stent-strut to the stent-strut width that is obtained from the stent information. The stent apposition value and an indicator for stent apposition level may be saved for the corresponding OCT image frame. Then, it may be determined whether the selected OCT image frame is the last OCT image frame, if the selected frame is the last frame, then the process ends. In this example the selected OCT image frame is the first OCT image frame, so a second OCT image frame is selected and the process returns to the aforementioned measure distance step. The process repeats until each OCT image frame selected is evaluated and a stent apposition value is obtained.

While GUI embodiment examples of the present disclosure show the angiography image on the left side of the GUI and an OCT image on the right side of the GUI, the orientation and location of the different imaging modalities may be changed or modified in one or more embodiments as desired by a user.

In one or more embodiments, the GUI may display one or more values (e.g., lumen area, mean diameter, min. diameter, max. diameter, etc.). Such information may be used to determine or decide how to plan or proceed with a procedure, e.g., what stent size to use when the procedure relates to expansion/underexpansion or apposition/malapposition.

As aforementioned, evaluating underexpansion/expansion and/or apposition/malapposition are examples of some of the applications of one or more embodiments of the present disclosure. One or more embodiments of the present disclosure may involve one or more additional or alternative applications, such as, but not limited to, determining whether plaque tissue, or a buildup of calcium, requires further attention. Another application example may involve determining whether a rotor blade needs to be fixed or not. Another application example may involve identifying or determining diagnosis information, determining whether medical attention is needed or not, identifying a region of choice or interest, etc. An indicator may be used to show or indicate one or more of such applications, such as, but not limited to, different bands, different band colors, etc.

One or more embodiments of the present disclosure may include taking multiple views (e.g., OCT image, ring view, tomo view, anatomical view, etc.), and one or more embodiments may highlight or emphasize NIRAF. In one or more embodiments, two handles may operate as endpoints that may bound the color extremes of the NIRAF data in or more embodiments. In one or more embodiments, the two handles may indicate a corresponding cut or area displayed in the 3D view.

In addition to the standard tomographic view, the user may select to display multiple longitudinal views. When connected to an angiography system, the Graphical User Interface (GUI) may also display angiography images.

In accordance with one or more aspects of the present disclosure, the aforementioned features are not limited to being displayed or controlled using any particular GUI. In general, the aforementioned imaging modalities may be used in various ways, including with or without one or more features of aforementioned embodiments of a GUI or GUIs. For example, a GUI may show an OCT image with a tool or marker to change the image view as aforementioned even if not presented with a GUI (or with one or more other components of a GUI; in one or more embodiments, the display may be simplified for a user to display set or desired information).

The procedure to select the region of interest and the position of a marker, an angle, a plane, etc., for example, using a touch screen, a GUI (or one or more components of a GUI; in one or more embodiments, the display may be simplified for a user to display the set or desired information), a processor (e.g., processor or computer 2, 1200, 1200', or any other processor discussed herein) may involve, in one or more embodiments, a single press with a finger and dragging on the area to make the selection or modification. The new orientation and updates to the view may be calculated upon release of a finger, or a pointer.

For one or more embodiments using a touch screen, two simultaneous touch points may be used to make a selection or modification, and may update the view based on calculations upon release.

One or more functions may be controlled with one of the imaging modalities, such as the angiography image view or the OCT image view, to centralize user attention, maintain focus, and allow the user to see all relevant information in a single moment in time.

In one or more embodiments, one imaging modality may be displayed or multiple imaging modalities may be displayed.

One or more procedures may be used in one or more embodiments to select a region of choice or a region of interest for a view. For example, after a single touch is made on a selected area (e.g., by using a touch screen, by using a mouse or other input device to make a selection, etc.), the semi-circle (or other geometric shape used for the designated area) may automatically adjust to the selected region of choice or interest. Two (2) single touch points may operate to connect/draw the region of choice or interest. A single touch on a tomo or tomographic view (e.g., the OCT view 403 or 603) may operate to sweep around the tomo view, and may connect to form the region of choice or interest.

Figure 9A:
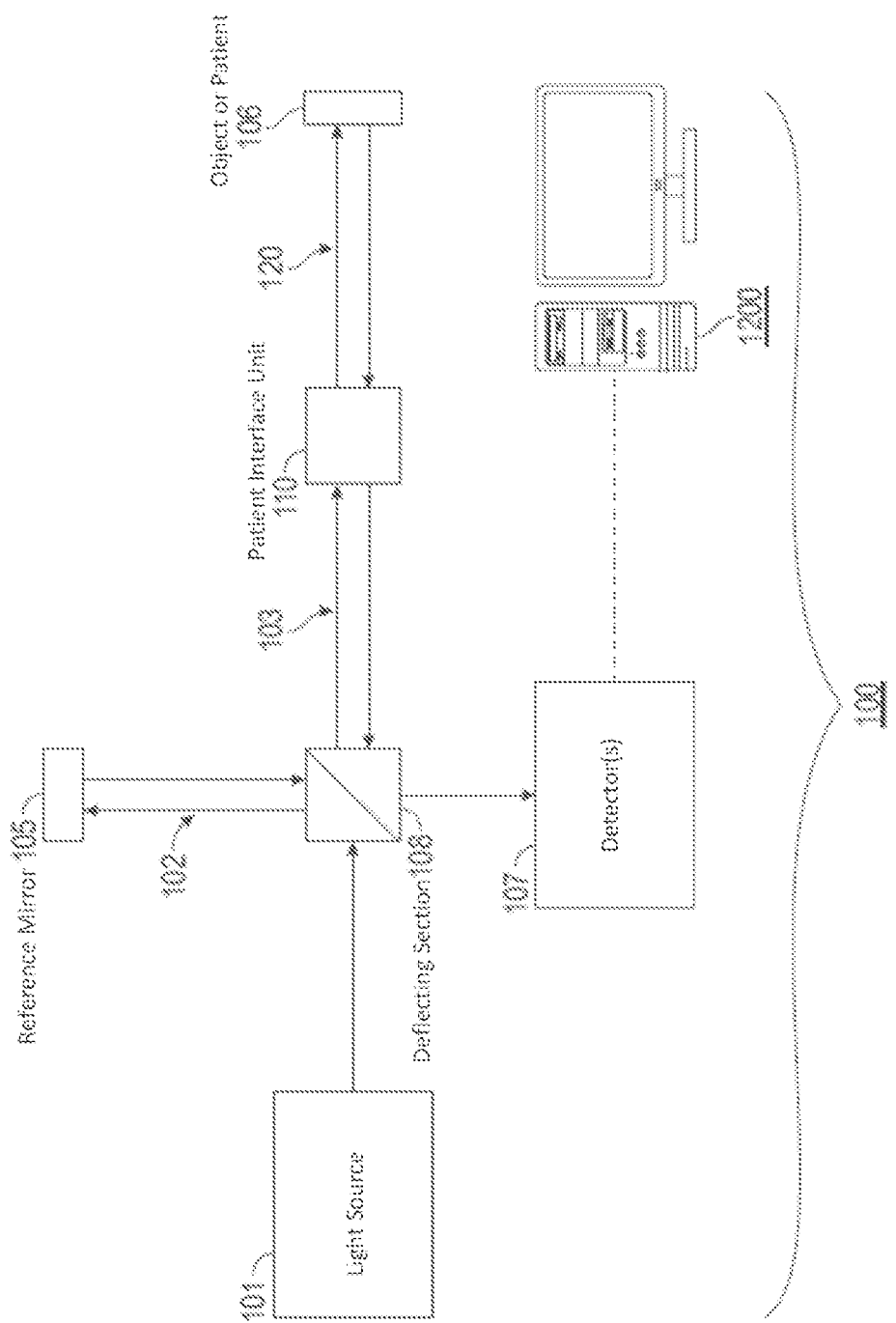
FIG. 9A shows at least one embodiment of an OCT apparatus or system for utilizing one or more imaging modalities for constructing and/or reconstructing 3D structure(s) in accordance with one or more aspects of the present disclosure.

FIG. 9A shows an OCT system 100 (as referred to herein as "system 100" or "the system 100") which may be used for multiple imaging modalities in accordance with one or more aspects of the present disclosure. The system 100 comprises a light source 101, a reference arm 102, a sample arm 103, a deflected or deflecting section 108, a reference mirror (also referred to as a "reference reflection", "reference reflector", "partially reflecting mirror" and a "partial reflector") 105, and one or more detectors 107 (which may be connected to a computer 1200). In one or more embodiments, the system 100 may include a patient interface device or unit ("PIU") no and a catheter 120 (see e.g., embodiment examples of a PIU and a catheter as shown in FIG. 1A, FIG. 4 and/or FIGS. 9A-9C), and the system 100 may interact with an object 106, a patient (e.g., a blood vessel of a patient) 106, etc. (e.g., via the catheter 120 and/or the PIU 110). In one or more embodiments, the system 100 includes an interferometer or an interferometer is defined by one or more components of the system 100, such as, but not limited to, at least the light source 101, the reference arm 102, the sample arm 103, the deflecting section 108 and the reference mirror 105.

Figure 9B:
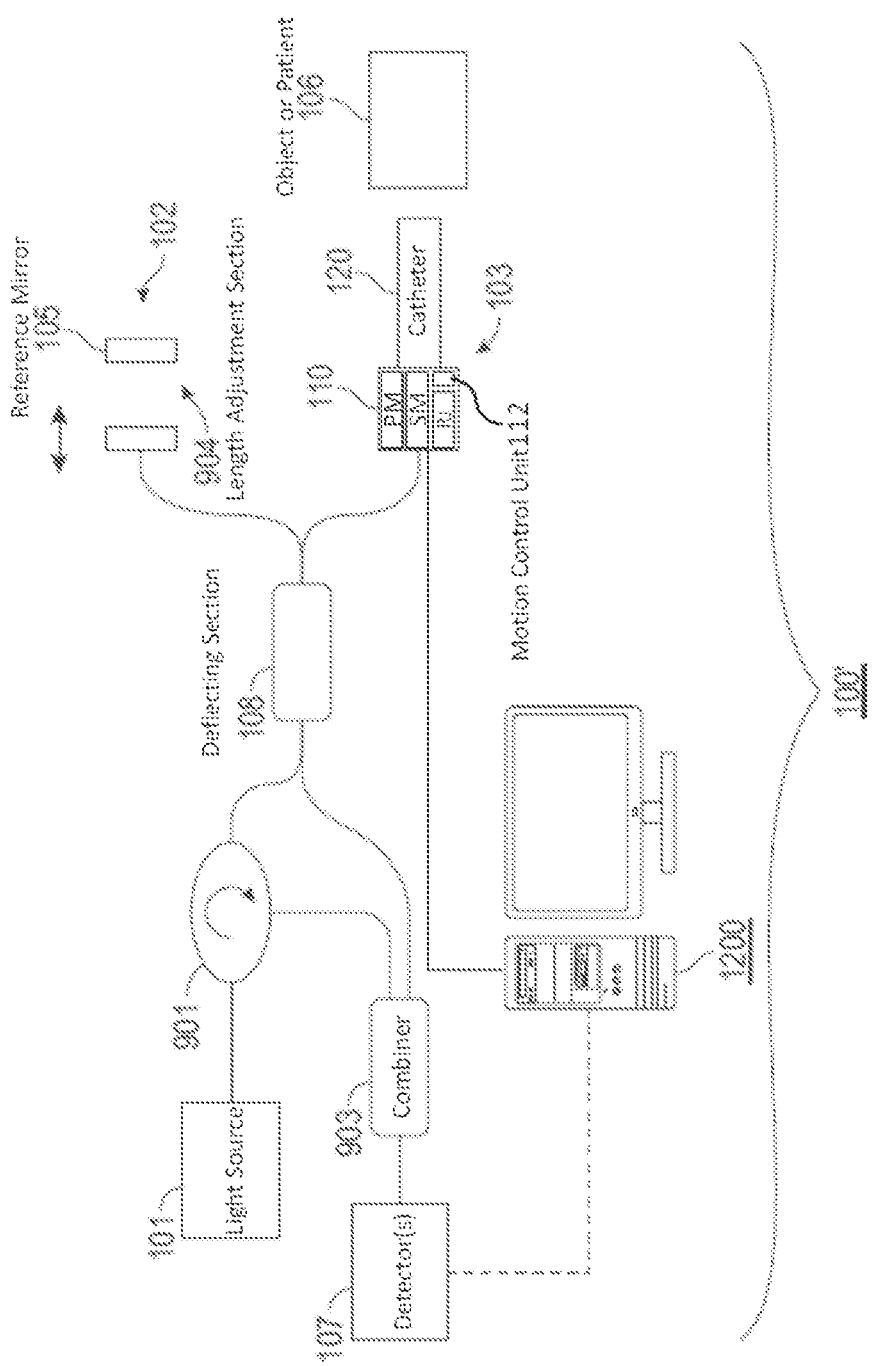
FIG. 9B shows at least another embodiment of an OCT apparatus or system for utilizing one or more imaging modalities for constructing and/or reconstructing 3D structure(s) in accordance with one or more aspects of the present disclosure.

In accordance with one or more further aspects of the present disclosure, bench top systems may be utilized with multiple imaging modalities as disclosed herein. FIG. 9B shows an example of a system that can utilize the multiple imaging modalities and related methods discussed herein for a bench-top such as for ophthalmic applications. A light from a light source 101 delivers and splits into a reference arm 102 and a sample arm 103 with a deflecting section 108. A reference beam goes through a length adjustment section 904 and is reflected from a reference mirror (such as or similar to the reference mirror or reference reflection 105 shown in FIG. 9A) in the reference arm 102 while a sample beam is reflected or scattered from an object, a patient (e.g., blood vessel of a patient), etc. 106 in the sample arm 103 (e.g., via the PIU no and the catheter 120). In one embodiment, both beams combine at the deflecting section 108 and generate interference patterns. In one or more embodiments, the beams go to the combiner 903, and the combiner 903 combines both beams via the circulator 901 and the deflecting section 108, and the combined beams are delivered to one or more detectors (such as the one or more detectors 107). The output of the interferometer is continuously acquired with one or more detectors, such as the one or more detectors 107. The electrical analog signals are converted to the digital signals to analyze them with a computer, such as, but not limited to, the computer 1200 (see FIGS. 9A-9C; also shown in FIG. 11 discussed further below), the computer 1200' (see e.g., FIG. 12 discussed further below), the computer 2 (see FIG. 1A), any other computer or processor discussed herein, etc. Additionally or alternatively, one or more of the computers, CPUs, processors, etc. discussed herein may be used to process, control, update, emphasize, and/or change one or more of imaging modalities, and/or process the related techniques, functions or methods, or may process the electrical signals as discussed above.

Figure 9C:
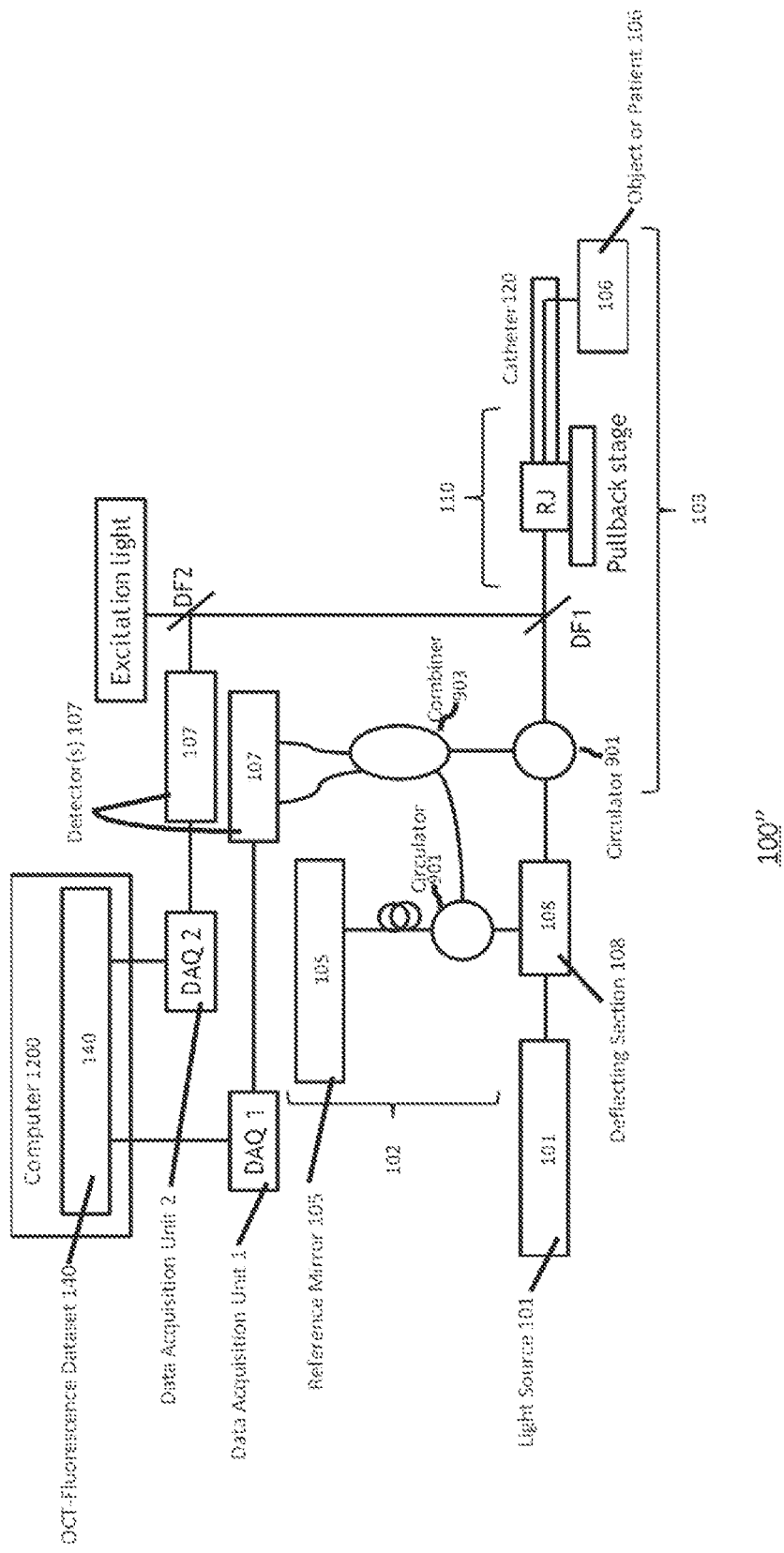
FIG. 9C shows at least a further embodiment of an OCT and NIRAF apparatus or system for utilizing one or more imaging modalities for constructing and/or reconstructing 3D structure(s) in accordance with one or more aspects of the present disclosure.

The electrical analog signals may be converted to the digital signals to analyze them with a computer, such as, but not limited to, the computer 1200 (see FIGS. 1B and 9A-9C; also shown in FIG. 11 discussed further below), the computer 1200' (see e.g., FIG. 12 discussed further below), the computer 2 (see FIG. 1A), any other processor or computer discussed herein, etc. Additionally or alternatively, one or more of the computers, CPUs, processors, etc. discussed herein may be used to process, control, update, emphasize, and/or change one or more imaging modalities, and/or process the related techniques, functions or methods, or may process the electrical signals as discussed above. In one or more embodiments (see e.g., FIG. 9B), the sample arm 103 includes the PIU no and the catheter 120 so that the sample beam is reflected or scattered from the object, patient (e.g., blood vessel of a patient), etc. 106 as discussed herein. In one or more embodiments, the PIU no may include one or more motors to control the pullback operation of the catheter 120 (or one or more components thereof) and/or to control the rotation or spin of the catheter 120 (or one or more components thereof) (see e.g., the motor M of FIG. 1B). For example, as best seen in FIG. 9B, the PIU no may include a pullback motor (PM) and a spin motor (SM), and/or may include a motion control unit 112 that operates to perform the pullback and/or rotation features using the pullback motor PM and/or the spin motor SM. As discussed herein, the PIU no may include a rotary junction (e.g., rotary junction RJ as shown in FIGS. 9B and 9C). The rotary junction RJ may be connected to the spin motor SM so that the catheter 120 may obtain one or more views or images of the object, patient (e.g., blood vessel of a patient), etc. 106. The computer 1200 (or the computer 1200', computer 2, any other computer or processor discussed herein, etc.) may be used to control one or more of the pullback motor PM, the spin motor SM and/or the motion control unit 112. An OCT system may include one or more of a computer (e.g., the computer 1200, the computer 1200', computer 2, any other computer or processor discussed herein, etc.), the PIU no, the catheter 120, a monitor (such as the display 1209), etc. One or more embodiments of an OCT system may interact with one or more external systems, such as, but not limited to, an angio system, external displays, one or more hospital networks, external storage media, a power supply, a bedside controller (e.g., which may be connected to the OCT system using Bluetooth technology or other methods known for wireless communication), etc.

In one or more embodiments including the deflecting or deflected section 108 (best seen in FIGS. 9A-9C), the deflected section 108 may operate to deflect the light from the light source 101 to the reference arm 102 and/or the sample arm 103, and then send light received from the reference arm 102 and/or the sample arm 103 towards the at least one detector 107 (e.g., a spectrometer, one or more components of the spectrometer, another type of detector, etc.). In one or more embodiments, the deflected section (e.g., the deflected section 108 of the system 100, 100', 100", any other system discussed herein, etc.) may include or may comprise one or more interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the interferometer or the optical interference system may include one or more components of the system 100 (or any other system discussed herein) such as, but not limited to, one or more of the light source 101, the deflected section 108, the rotary junction RJ, a PIU 110, a catheter 120, etc. One or more features of the aforementioned configurations of at least FIGS. 1A-12 may be incorporated into one or more of the systems, including, but not limited to, the system 100, 100', 100", discussed herein.

In accordance with one or more further aspects of the present disclosure, one or more other systems may be utilized with one or more of the multiple imaging modalities and related method(s) as disclosed herein. FIG. 9C shows an example of a system 100" that may utilize the one or more multiple imaging modalities and/or related technique(s) or method(s) such as for ophthalmic applications. FIG. 9C shows an exemplary schematic of an OCT-fluorescence imaging system 100", according to one or more embodiments of the present disclosure. An OCT light source 101 (e.g., with a 1.3 µm) is delivered and split into a reference arm 102 and a sample arm 103 with a deflector or deflected section (e.g., a splitter) 108, creating a reference beam and sample beam, respectively. The reference beam from the OCT light source 101 is reflected by a reference mirror 105 while a sample beam is reflected or scattered from an object (e.g., an object to be examined, an object, a patient, etc.) 106 through a circulator 901, a rotary junction 90 ("RJ") and a catheter 120. In one or more embodiments, the fiber between the circulator 901 and the reference mirror or reference reflection 105 may be coiled to adjust the length of the reference arm 102 (best seen in FIG. 9C). Optical fibers in the sample arm 103 may be made of double clad fiber ("DCF"). Excitation light for the fluorescence may be directed to the RJ 90 and the catheter 120, and illuminate the object (e.g., an object to be examined, an object, a patient, etc.) 106. The light from the OCT light source 101 may be delivered through the core of DCF while the fluorescence light emitted from the object (e.g., an object to be examined, an object, a patient, etc.) 106 may be collected through the cladding of the DCF. For pullback imaging, the RJ 90 may be moved with a linear stage to achieve helical scanning of the object (e.g., an object to be examined, an object, a patient, etc.) 106. In one or more embodiments, the RJ 90 may include any one or more features of an RJ as discussed herein. Dichroic filters DF1, DF2 may be used to separate excitation light and the rest of fluorescence and OCT lights. For example (and while not limited to this example), in one or more embodiments, DF1 may be a long pass dichroic filter with a cutoff wavelength of ~1000 nm, and the OCT light, which may be longer than a cutoff wavelength of DF1, may go through the DF1 while fluorescence excitation and emission, which are a shorter wavelength than the cut off, reflect at DF1. In one or more embodiments, for example (and while not limited to this example), DF2 may be a short pass dichroic filter; the excitation wavelength may be shorter than fluorescence emission light such that the excitation light, which has a wavelength shorter than a cutoff wavelength of DF2, may pass through the DF2, and the fluorescence emission light reflect with DF2. In one embodiment, both beams combine at the deflecting section 108 and generate interference patterns. In one or more embodiments, the beams go to the coupler or combiner 903, and the coupler or combiner 903 combines both beams via the circulator 901 and the deflecting section 108, and the combined beams are delivered to one or more detectors (such as the one or more detectors 107; see e.g., the first detector 107 connected to the coupler or combiner 903 in FIG. 9C).

In one or more embodiments, the optical fiber in the catheter 120 operates to rotate inside the catheter 120, and the OCT light and excitation light may be emitted from a side angle of a tip of the catheter 120. After interacting with the object or patient 106, the OCT light may be delivered back to an OCT interferometer (e.g., via the circulator 901 of the sample arm 103), which may include the coupler or combiner 903, and combined with the reference beam (e.g., via the coupler or combiner 903) to generate interference patterns. The output of the interferometer is detected with a first detector 107, wherein the first detector 107 may be photodiodes or multi-array cameras, and then may be recorded to a computer (e.g., to the computer 2, the computer 1200 as shown in FIG. 9C, the computer 1200', or any other computer discussed herein) through a first data-acquisition unit or board ("DAQ1").

Simultaneously or at a different time, the fluorescence intensity may be recorded through a second detector 107 (e.g., a photomultiplier) through a second data-acquisition unit or board ("DAQ2"). The OCT signal and fluorescence signal may be then processed by the computer (e.g., to the computer 2, the computer 1200 as shown in FIG. 9C, the computer 1200', or any other computer discussed herein) to generate an OCT-fluorescence dataset 140, which includes or is made of multiple frames of helically scanned data. Each set of frames includes or is made of multiple data elements of co-registered OCT and fluorescence data, which correspond to the rotational angle and pullback position.

Detected fluorescence or auto-fluorescence signals may be processed or further processed as discussed in U.S. Pat. App. No. 62/861,888, filed on Jun. 14, 2019, the disclosure of which is incorporated herein by reference in its entirety, and/or as discussed in U.S. patent application Ser. No. 16/368,510, filed Mar. 28, 2019, and published as U.S. Pat. Pub. No. 2019/0298174 on Oct. 3, 2019, the disclosure of which is incorporated herein by reference herein in its entirety.

While not limited to such arrangements, configurations, devices or systems, one or more embodiments of the devices, apparatuses, systems, methods, storage mediums, GUI's, etc. discussed herein may be used with an apparatus or system as aforementioned, such as, but not limited to, for example, the system 100, the system 100', the system 100", the devices, apparatuses, or systems of FIGS. 1A-12, any other device, apparatus or system discussed herein, etc. In one or more embodiments, one user may perform the method(s) discussed herein. In one or more embodiments, one or more users may perform the method(s) discussed herein. In one or more embodiments, one or more of the computers, CPUs, processors, etc. discussed herein may be used to process, control, update, emphasize, and/or change one or more of the imaging modalities, and/or process the related techniques, functions or methods, or may process the electrical signals as discussed above.

The light source 101 may include a plurality of light sources or may be a single light source. The light source 101 may be a broadband lightsource, and may include one or more of a laser, an organic light emitting diode (OLED), a light emitting diode (LED), a halogen lamp, an incandescent lamp, supercontinuum light source pumped by a laser, and/or a fluorescent lamp. The light source 101 may be any light source that provides light which may then be dispersed to provide light which is then used for imaging, performing control, viewing, changing, emphasizing methods for imaging modalities, constructing or reconstructing 3D structure(s), and/or any other method discussed herein. The light source 101 may be fiber coupled or may be free space coupled to the other components of the apparatus and/or system 100, 100', 100", the devices, apparatuses or systems of FIGS. 1A-12, or any other embodiment discussed herein. As aforementioned, the light source 101 may be a swept-source (SS) light source.

Additionally or alternatively, the one or more detectors 107 may be a linear array, a charge-coupled device (CCD), a plurality of photodiodes or some other method of converting the light into an electrical signal. The detector(s) 107 may include an analog to digital converter (ADC). The one or more detectors may be detectors having structure as shown in one or more of FIGS. 1A-12 and as discussed above.

Figure 10:
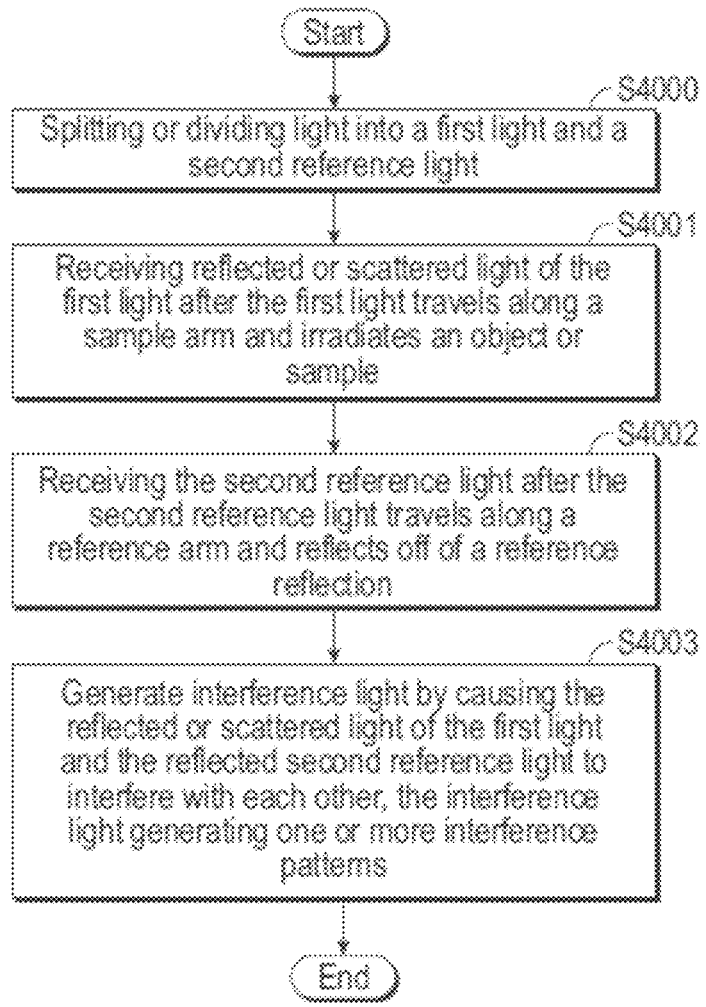
FIG. 10 is a flow diagram showing a method of performing an imaging feature, function or technique in accordance with one or more aspects of the present disclosure.

In accordance with one or more aspects of the present disclosure, one or more methods for performing imaging are provided herein. FIG. 10 illustrates a flow chart of at least one embodiment of a method for performing imaging. The method(s) may include one or more of the following: (i) splitting or dividing light into a first light and a second reference light (see step S4000 in FIG. 10); (ii) receiving reflected or scattered light of the first light after the first light travels along a sample arm and irradiates an object (see step S4001 in FIG. 10); (iii) receiving the second reference light after the second reference light travels along a reference arm and reflects off of a reference reflection (see step S4002 in FIG. 10); and (iv) generating interference light by causing the reflected or scattered light of the first light and the reflected second reference light to interfere with each other (for example, by combining or recombining and then interfering, by interfering, etc.), the interference light generating one or more interference patterns (see step S4003 in FIG. 10). One or more methods may further include using low frequency monitors to update or control high frequency content to improve image quality. For example, one or more embodiments may use multiple imaging modalities, related methods or techniques for same, etc. to achieve improved image quality. In one or more embodiments, an imaging probe may be connected to one or more systems (e.g., the system 100, the system 100', the system 100", the devices, apparatuses or systems of FIGS. 1A-12, any other system or apparatus discussed herein, etc.) with a connection member or interface module. For example, when the connection member or interface module is a rotary junction for an imaging probe, the rotary junction may be at least one of: a contact rotary junction, a lenseless rotary junction, a lens-based rotary junction, or other rotary junction known to those skilled in the art. The rotary junction may be a one channel rotary junction or a two channel rotary junction. In one or more embodiments, the illumination portion of the imaging probe may be separate from the detection portion of the imaging probe. For example, in one or more applications, a probe may refer to the illumination assembly, which includes an illumination fiber (e.g., single mode fiber, a GRIN lens, a spacer and the grating on the polished surface of the spacer, etc.). In one or more embodiments, a scope may refer to the illumination portion which, for example, may be enclosed and protected by a drive cable, a sheath, and detection fibers (e.g., multimode fibers (MMFs)) around the sheath. Grating coverage is optional on the detection fibers (e.g., MMFs) for one or more applications. The illumination portion may be connected to a rotary joint and may be rotating continuously at video rate. In one or more embodiments, the detection portion may include one or more of: a detection fiber, a detector (e.g., the one or more detectors 107, a spectrometer, etc.), the computer 1200, the computer 1200', the computer 2, any other computer or processor discussed herein, etc. The detection fibers may surround the illumination fiber, and the detection fibers may or may not be covered by a grating, a spacer, a lens, an end of a probe or catheter, etc.

The one or more detectors 107 may transmit the digital or analog signals to a processor or a computer such as, but not limited to, an image processor, a processor or computer 1200, 1200' (see e.g., FIGS. 9A-9C and 11-12), a computer 2 (see e.g., FIG. 1A), any other processor or computer discussed herein, a combination thereof, etc. The image processor may be a dedicated image processor or a general purpose processor that is configured to process images. In at least one embodiment, the computer 1200, 1200', 2 or any other processor or computer discussed herein may be used in place of, or in addition to, the image processor. In an alternative embodiment, the image processor may include an ADC and receive analog signals from the one or more detectors 107. The image processor may include one or more of a CPU, DSP, FPGA, ASIC, or some other processing circuitry. The image processor may include memory for storing image, data, and instructions. The image processor may generate one or more images based on the information provided by the one or more detectors 107. A computer or processor discussed herein, such as, but not limited to, a processor of the devices, apparatuses or systems of FIGS.

1A-9C, the computer 1200, the computer 1200', the computer 2, the image processor, may also include one or more components further discussed herein below (see e.g., FIGS. 11-12).

Figure 11:
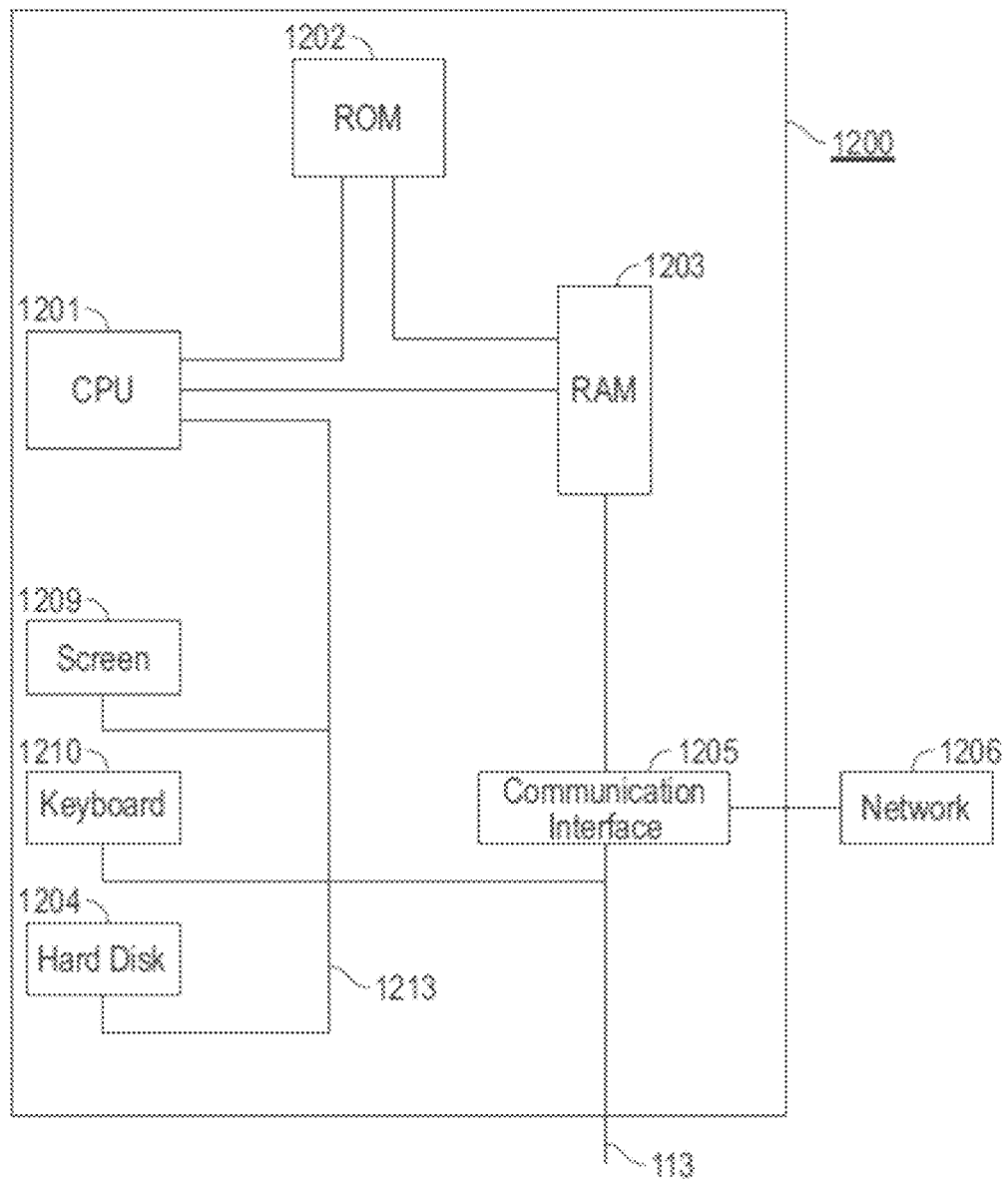
FIG. 11 shows a schematic diagram of an embodiment of a computer that may be used with one or more embodiments of an apparatus or system or one or more methods discussed herein in accordance with one or more aspects of the present disclosure.
Figure 12:
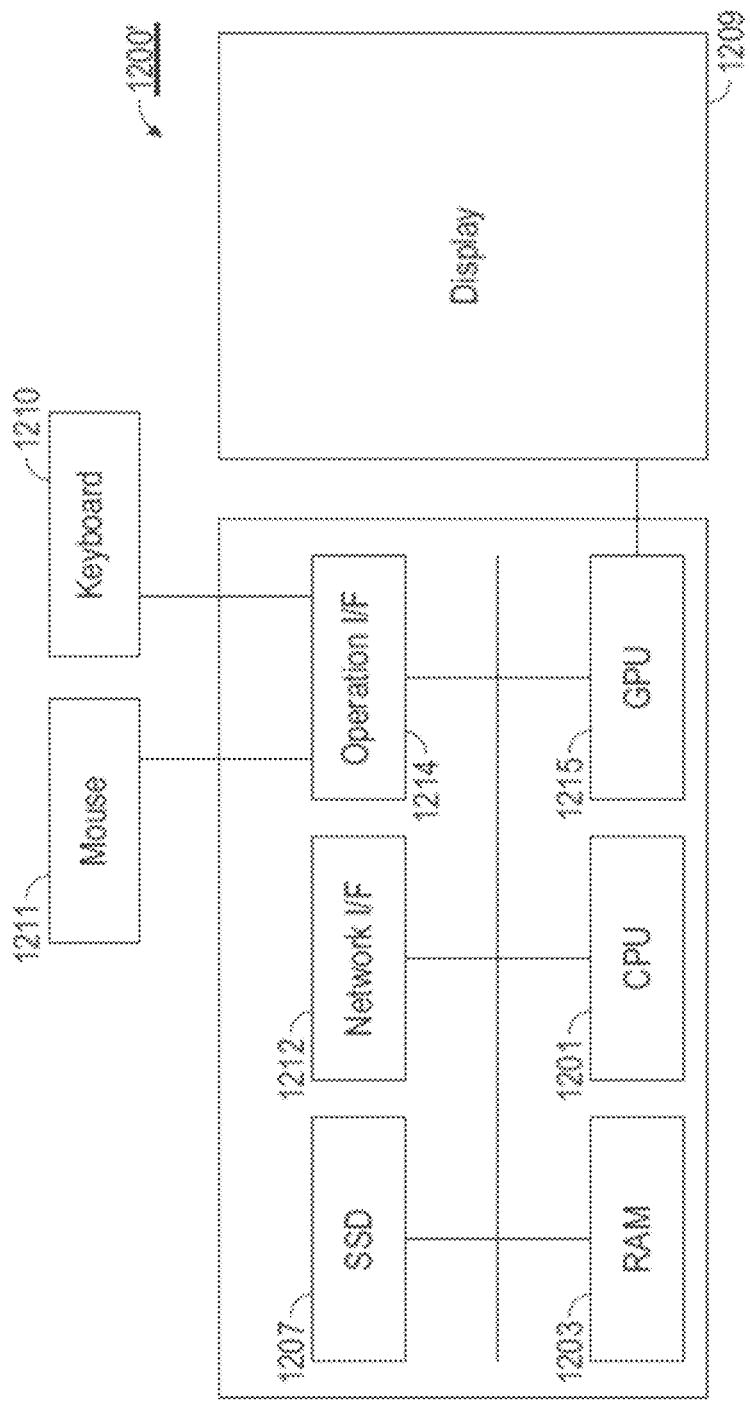
FIG. 12 shows a schematic diagram of another embodiment of a computer that may be used with one or more embodiments of an imaging apparatus or system or methods discussed herein in accordance with one or more aspects of the present disclosure.

In at least one embodiment, a console or computer 1200, 1200', a computer 2, any other computer or processor discussed herein, etc. operates to control motions of the RJ via the motion control unit (MCU) 112 or a motor M, acquires intensity data from the detector(s) in the one or more detectors 107, and displays the scanned image (e.g., on a monitor or screen such as a display, screen or monitor 1209 as shown in the console or computer 1200 of any of FIGS. 9A-9C and FIG. 11 and/or the console 1200' of FIG. 12 as further discussed below; the computer 2 of FIG. 1A; any other computer or processor discussed herein; etc.). In one or more embodiments, the MCU 112 or the motor M operates to change a speed of a motor of the RJ and/or of the RJ. The motor may be a stepping or a DC servo motor to control the speed and increase position accuracy (e.g., compared to when not using a motor, compared to when not using an automated or controlled speed and/or position change device, compared to a manual control, etc.).

The output of the one or more components of any of the systems discussed herein may be acquired with the at least one detector 107, e.g., such as, but not limited to, photodiodes, Photomultiplier tube(s) (PMTs), line scan camera(s), or multi-array camera(s). Electrical analog signals obtained from the output of the system 100, 100', 100", and/or the detector(s) 107 thereof, and/or from the devices, apparatuses, or systems of FIGS. 1A-9C, are converted to digital signals to be analyzed with a computer, such as, but not limited to, the computer 1200, 1200'. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Unless otherwise discussed herein, like numerals indicate like elements. For example, while variations or differences exist between the systems, such as, but not limited to, the system 100, the system 100', the system 100", or any other device, apparatus or system discussed herein, one or more features thereof may be the same or similar to each other, such as, but not limited to, the light source 101 or other component(s) thereof (e.g., the console 1200, the console 1200', etc.). Those skilled in the art will appreciate that the light source 101, the motor or MCU 112, the RJ, the at least one detector 107, and/or one or more other elements of the system 100 may operate in the same or similar fashion to those like-numbered elements of one or more other systems, such as, but not limited to, the devices, apparatuses or systems of FIGS. 1A-9C, the system 100', the system 100", or any other system discussed herein. Those skilled in the art will appreciate that alternative embodiments of the devices, apparatuses or systems of FIGS. 1A-9C, the system 100', the system 100", any other device, apparatus or system discussed herein, etc., and/or one or more like-numbered elements of one of such systems, while having other variations as discussed herein, may operate in the same or similar fashion to the like-numbered elements of any of the other systems (or components thereof) discussed herein. Indeed, while certain differences exist between the system 100 of FIG. 9A and one or more embodiments shown in any of FIGS. 1A-8 and 9B-9C, for example, as discussed herein, there are similarities. Likewise, while the console or computer 1200 may be used in one or more systems (e.g., the system 100, the system 100', the system 100", the devices, apparatuses or systems of any of FIGS. 1A-12, or any other system discussed herein, etc.), one or more other consoles or computers, such as the console or computer 1200', any other computer or processor discussed herein, etc., may be used additionally or alternatively.

There are many ways to compute intensity, viscosity, resolution (including increasing resolution of one or more images), etc., to use one or more imaging modalities, to construct or reconstruct 3D structure(s), and/or related methods for same, discussed herein, digital as well as analog. In at least one embodiment, a computer, such as the console or computer 1200, 1200', may be dedicated to control and monitor the imaging (e.g., OCT, single mode OCT, multi-modal OCT, multiple imaging modalities, etc.) devices, systems, methods and/or storage mediums described herein.

The electric signals used for imaging may be sent to one or more processors, such as, but not limited to, a computer or processor 2 (see e.g., FIG. 1A), a computer 1200 (see e.g., FIGS. 9A-9B and 11), a computer 1200' (see e.g., FIG. 12), etc. as discussed further below, via cable(s) or wire(s), such as, but not limited to, the cable(s) or wire(s) 113 (see FIG. 11). Additionally or alternatively, the electric signals, as aforementioned, may be processed in one or more embodiments as discussed above by any other computer or processor or components thereof. The computer or processor 2 as shown in FIG. 1A may be used instead of any other computer or processor discussed herein (e.g., computer or processors 1200, 1200', etc.), and/or the computer or processor 1200, 1200' may be used instead of any other computer or processor discussed herein (e.g., computer or processor 2). In other words, the computers or processors discussed herein are interchangeable, and may operate to perform any of the multiple imaging modalities feature(s) and method(s) discussed herein, including using, controlling, and changing a GUI or multiple GUI's.

Various components of a computer system 1200 are provided in FIG. 11. A computer system 1200 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS (or "Bus") or other connection lines (e.g., connection line 1213) between one or more of the aforementioned components (e.g., including but not limited to, being connected to the console, the probe, the imaging apparatus or system, any motor discussed herein, a light source, etc.). In addition, the computer system 1200 may comprise one or more of the aforementioned components. For example, a computer system 1200 may include a CPU 1201, a RAM 1203, an input/output (I/O) interface (such as the communication interface 1205) and a bus (which may include one or more lines 1213 as a communication system between components of the computer system 1200; in one or more embodiments, the computer system 1200 and at least the CPU 1201 thereof may communicate with the one or more aforementioned components of a device or system, such as, but not limited to, an apparatus or system using one or more imaging modalities and related method(s) as discussed herein), and one or more other computer systems 1200 may include one or more combinations of the other aforementioned components (e.g., the one or more lines 1213 of the computer 1200 may connect to other components via line 113). The CPU 1201 is configured to read and perform computer-executable instructions stored in a storage medium. The computer-executable instructions may include those for the performance of the methods and/or calculations described herein. The system 1200 may include one or more additional processors in addition to CPU 1201, and such processors, including the CPU 1201, may be used for tissue or object characterization, diagnosis, evaluation, imaging and/or construction or reconstruction. The system 1200 may further include one or more processors connected via a network connection (e.g., via network 1206). The CPU 1201 and any additional processor being used by the system 1200 may be located in the same telecom network or in different telecom networks (e.g., performing feature(s), function(s), technique(s), method(s), etc. discussed herein may be controlled remotely).

The I/O or communication interface 1205 provides communication interfaces to input and output devices, which may include a light source, a spectrometer, a microphone, a communication cable and a network (either wired or wireless), a keyboard 1210, a mouse (see e.g., the mouse 1211 as shown in FIG. 12), a touch screen or screen 1209, a light pen and so on. The communication interface of the computer 1200 may connect to other components discussed herein via line 113 (as diagrammatically shown in FIG. 11). The Monitor interface or screen 1209 provides communication interfaces thereto.

Any methods and/or data of the present disclosure, such as the methods for performing tissue or object characterization, diagnosis, examination, imaging (including, but not limited to, increasing image resolution, performing imaging using one or more imaging modalities, viewing or changing one or more imaging modalities and related methods (and/or option(s) or feature(s)), etc.), and/or construction or reconstruction, for example, as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-Ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 12), SRAM, etc.), an optional combination thereof, a server/database, etc. may be used to cause a processor, such as, the processor or CPU 1201 of the aforementioned computer system 1200 to perform the steps of the methods disclosed herein. The computer-readable storage medium may be a non-transitory computer-readable medium, and/or the computer-readable medium may comprise all computer-readable media, with the sole exception being a transitory, propagating signal in one or more embodiments. The computer-readable storage medium may include media that store information for predetermined, limited, or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 1200, etc., as described above may be achieved utilizing suitable hardware, such as that illustrated in the figures. Functionality of one or more aspects of the present disclosure may be achieved utilizing suitable hardware, such as that illustrated in FIG. 11. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 11), the processor or computer 2 (as shown in FIG. 1A) and/or the computer or processor 1200' (as shown in FIG. 12) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium. The computers or processors (e.g., 2, 1200, 1200', etc.) may include the aforementioned CPU structure, or may be connected to such CPU structure for communication therewith.

As aforementioned, hardware structure of an alternative embodiment of a computer or console 1200' is shown in FIG. 12. The computer 1200' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. The computer or console 1200' may include a display 1209. The computer 1200' may connect with a motor, a console, or any other component of the device(s) or system(s) discussed herein via the operation interface 1214 or the network interface 1212 (e.g., via a cable or fiber, such as the cable or fiber 113 as similarly shown in FIG. 11). A computer, such as the computer 1200', may include a motor or motion control unit (MCU) in one or more embodiments. The operation interface 1214 is connected with an operation unit such as a mouse device 1211, a keyboard 1210 or a touch panel device. The computer 1200' may include two or more of each component.

At least one computer program is stored in the SSD 1207, and the CPU 1201 loads the at least one program onto the RAM 1203, and executes the instructions in the at least one program to perform one or more processes described herein, as well as the basic input, output, calculation, memory writing and memory reading processes.

The computer, such as the computer 2, the computer 1200, 1200', (or other component(s) such as, but not limited to, the PCU, etc.), etc. may communicate with an MCU, an interferometer, a spectrometer, a detector, etc. to perform imaging, and reconstructs an image from the acquired intensity data. The monitor or display 1209 displays the reconstructed image, and may display other information about the imaging condition or about an object to be imaged. The monitor 1209 also provides a graphical user interface for a user to operate any system discussed herein. An operation signal is input from the operation unit (e.g., such as, but not limited to, a mouse device 1211, a keyboard 1210, a touch panel device, etc.) into the operation interface 1214 in the computer 1200', and corresponding to the operation signal the computer 1200' instructs any system discussed herein to set or change the imaging condition (e.g., improving resolution of an image or images), and to start or end the imaging. A light or laser source and a spectrometer and/or detector may have interfaces to communicate with the computers 1200, 1200' to send and receive the status information and the control signals.

Similarly, the present disclosure and/or one or more components of devices, systems and storage mediums, and/or methods, thereof also may be used in conjunction with optical coherence tomography probes. Such probes include, but are not limited to, the OCT imaging systems disclosed in U.S. Pat. Nos. 6,763,261; 7,366,376; 7,843,572; 7,872,759; 8,289,522; 8,676,013; 8,928,889; 9,087,368; 9,557,154; and U.S. Pat. Pub. Nos. 2014/0276011 and 2017/0135584; and WO 2016/015052 to Tearney et al. and arrangements and methods of facilitating photoluminescence imaging, such as those disclosed in U.S. Pat. No. 7,889,348 to Tearney et al., as well as the disclosures directed to multimodality imaging disclosed in U.S. Pat. No. 9,332,942, and U.S. Patent Publication Nos. 2010/0092389, 2011/0292400, 2012/0101374, and 2016/0228097, and WO 2016/144878, each of which patents and patent publications are incorporated by reference herein in their entireties.

Although the disclosure herein has been described with reference to particular embodiments, it is to be understood that these embodiments are merely illustrative of the principles and applications of the present disclosure (and are not limited thereto), and the invention is not limited to the disclosed embodiments. It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. An image processing apparatus comprising:
one or more processors that operate to:
obtain an angiography image of an object;
obtain an intravascular image at an acquisition location that is within at least a portion of the object, wherein the angiography image is obtained before the obtaining of the intravascular image, after the obtaining of the intravascular image, or simultaneously with the obtaining of the intravascular image;
display an image for each of multiple imaging modalities on a display, the multiple imaging modalities including at least an imaging modality for the intravascular image and an imaging modality for the angiography image;
determine the acquisition location of the intravascular image in the object within the angiography image;
determine an in-plane orientation of the intravascular image based on the intravascular image and the angiography image and based on a curvature by selecting one of a manual in-plane orientation determination and an automatic in-plane orientation determination, the in-plane orientation being a rotational orientation of the intravascular image in a plane that is vertical to a co-registration path and/or a longitudinal direction of the object, wherein the manual and/or automatic determination of the in-plane orientation uses: (i) information of the curvature and information of one or more side branches of the object, or (ii) information of the curvature, information of one or more side branches of the object, and a target of or in the object and a location of the target for a boundary condition;
in a case where the manual in-plane orientation determination is selected, use the manual in-plane orientation determination by receiving a manually input rotation angle number and/or selecting an input rotation angle that is used to place an intravascular frame on the co-registration path or a co-registration path plane, and using or receiving a manually input frame number to change the display to show an intravascular frame corresponding to the manually input frame number for performance of the in-plane orientation determination, and/or, in a case where the automatic in-plane orientation determination is selected, use the automatic in-plane orientation determination by performing the in-plane orientation determination automatically based on the intravascular image and the angiography image and based on the curvature;
register the intravascular image to the angiography image based on the determined acquisition location and the determined in-plane orientation; and
change or update the display for each of the multiple imaging modalities based on the in-plane orientation information and/or based on a request to update or change the in-plane orientation.

2. The apparatus of claim 1, wherein the one or more processors further operate to one or more of the following:
co-register the obtained angiography image and the obtained intravascular image;
determine whether a Percutaneous Coronary Intervention (PCI) is needed for the object;
in a case where it is determined that the object needs the PCI, perform the PCI, obtain one or more additional angiography and/or intravascular images, and perform the determining of the acquisition location, the determining of the in-plane orientation, and the registering for the one or more additional angiography and/or intravascular images, or, in a case where it is determined that the object does not need the PCI, save the images;
in a case where the PCI is to be performed, plan the PCI;
in a case where the PCI is performed, assess or evaluate procedural success of the PCI;
evaluate the physiology of the object; and/or
in a case where the object is a vessel or blood vessel, evaluate the physiology of the vessel and/or a lesion of the vessel.

3. The apparatus of claim 1, wherein the object is a blood vessel, and the acquisition location is a region that is diseased and/or is a region that a physician(s), clinician(s) or other user(s) of the apparatus is/are considering for further assessment.

4. The apparatus of claim 1, wherein the one or more processors further operate to one or more of the following:
co-register the obtained angiography image and the obtained intravascular image, and obtain one or more additional angiography and/or intravascular images, wherein the obtained intravascular image and/or the obtained one or more additional intravascular images include an obtained one or more Optical Coherence Tomography (OCT) or Intravascular Ultrasound (IVUS) images or frames;
obtain information from the one or more OCT or IVUS images or frames of one or more of the following: a type of the target and the location of the target where the target is a plaque, a lumen shape and/or a lumen size, and the one or more side branches of the object, wherein the object is a blood vessel;
determine the in-plane orientation of each OCT or IVUS frame using information of the curvature, the one or more side branches, and a lumen shape and/or size based on information from both one or more OCT or IVUS images or frames and the angiography image or images;
construct or reconstruct a three-dimensional (3D) structure of the object; and/or
use the constructed or reconstructed 3D structure for one or more of visualization, Percutaneous Coronary Intervention (PCI) planning, PCI performance, and physiological assessment.

5. The apparatus of claim 4, wherein the one or more processors further operate to one or more of the following:
determine OCT or IVUS frame orientation relative to the co-registration path using side branch location information relative to a main branch or a predetermined branch of the blood vessel;
display an option to perform the construction or reconstruction of a 3D structure on a display of the device;
display buttons, choices or options to select one of the manual in-plane orientation determination and automatic in-plane orientation determination;
in a case where the manual in-plane orientation determination is selected, use the manual in-plane orientation determination by receiving a manually input rotation angle number and/or select an input rotation angle that is used to place an OCT or IVUS frame on the co-registration path or the co-registration path plane, and using or receiving a manually input frame number to change the display to show the OCT or IVUS frame corresponding to the manually input frame number for performance of the in-plane orientation determination; and/or
in a case where the automatic in-plane orientation determination is selected, use the automatic in-plane orientation determination by performing the in-plane orientation determination automatically based on the intravascular image or the obtained one or more Optical Coherence Tomography (OCT) or Intravascular Ultrasound (IVUS) images or frames and based on the angiography image or images.

6. The apparatus of claim 1, wherein one or more of the following:
(i) the multiple imaging modalities include two or more of the following: a modality for a tomography image; a modality for an Optical Coherence Tomography (OCT) image; a modality for an auto-fluorescence image; a modality for a fluorescence image; a modality for a near-infrared auto-fluorescence (NIRAF) image; a modality for a near-infrared auto-fluorescence (NIRAF) image in a predetermined view, a carpet view, and/or an indicator view; a modality for a near-infrared fluorescence (NIRF) image; a modality for a near-infrared fluorescence (NIRF) image in a predetermined view, a carpet view, and/or an indicator view; a modality for a three-dimensional (3D) rendering; a modality for a 3D rendering of a vessel; a modality for a 3D rendering of a vessel in a half-pipe view or display; a modality for a 3D rendering of the object; a modality for a lumen profile; a modality for a lumen diameter display; a modality for a longitudinal view; computer tomography (CT); Magnetic Resonance Imaging (MRI); Intravascular Ultrasound (IVUS); a modality for an X-ray image or view; and a modality for an angiography view; and/or
(ii) the multiple imaging modalities include three or more of the following: a modality for a tomography image; a modality for an OCT image; a modality for an auto-fluorescence image; a modality for a fluorescence image; a modality for a near-infrared auto-fluorescence (NIRAF) image; a modality for a near-infrared auto-fluorescence (NIRAF) image in a predetermined view, a carpet view, and/or an indicator view; a modality for a near-infrared fluorescence (NIRF) image; a modality for a near-infrared fluorescence (NIRF) image in a predetermined view, a carpet view, and/or an indicator view; a modality for a 3D rendering; a modality for a 3D rendering of a vessel; a modality for a 3D rendering of a vessel in a half-pipe view or display; a modality for a 3D rendering of the object; a modality for a lumen profile; a modality for a lumen diameter display; a modality for a longitudinal view; CT; MRI; IVUS; a modality for an X-ray image or review; and a modality for an angiography view.

7. The apparatus of claim 1, wherein the one or more processors further operate to one or more of the following:
(i) receive information for an interventional device to be used for a Percutaneous Coronary Intervention (PCI); and/or
(ii) in a case where the interventional device is a stent, perform one or more of: detecting stent expansion or underexpansion, detecting stent apposition or malapposition, performing co-registration, performing imaging, displaying a notification regarding the detected stent expansion or underexpansion, and displaying a notification regarding the detected stent apposition or malapposition.

8. The apparatus of claim 1, wherein the one or more processors operate to one or more of the following:
(i) employ information on a two-dimensional (2D) and/or three-dimensional (3D) structure or structures for the object to create or construct/reconstruct a computational fluid dynamics (CFD) model or result for the object;
(ii) use 2D or 3D results and/or 2D or 3D structure(s) and calculate fractional flow reserve (FFR) and/or instantaneous wave-free ratio (iFR);
(iii) employ CFD to calculate one or more pressures and to have or obtain the FFR and/or the iFR;
(iv) calculate the FFR and provide information on treatment option(s) for the treatment of stenosis and/or another medical condition;
(v) use the FFR and/or the iFR in real-time;
(vi) calculate pressure(s) and include a lamp parameter/circuit analog model;

(vii) include or use an Optical Coherence Tomography (OCT) or Intravascular Ultrasound (IVUS) images or frames FFR method that uses anatomic information; and/or
(viii) the anatomic information includes at least a volume of a vessel.

9. The apparatus of claim 1, further comprising a touch screen, wherein the one or more processors further operate to one or more of the following:
   detect a selected region of interest, via an input received through or with the touch screen;
   detect an input update request via a single press/touch and drag with a finger or tool of a user over an area of the touch screen to change or update one or more of the views or images;
   detect an input update request via two simultaneous touch points made on the at least one imaging modality view or image and redraw the image of the at least one imaging modality such that a control bar or tool having two handles defines the redrawn image where both of the two handles align near or on an arc of the redrawn image based on the two touch points, and calculate and update the new orientation/position of the at least one imaging modality image or view based upon a release of the two touch points; and/or
   detect two simultaneous touch points, made by fingers or tools of the user, made on the at least one imaging modality showing a tomographic image or an Optical Coherence Tomography (OCT) image, where the fingers or the tools are held in place, and the two touch points are swept around the tomographic image or the OCT image in a circular motion that moves a rotational control bar displayed on the at least one imaging modality, and calculate and update the new orientation/position of the at least one imaging modality image or view based upon a release of the two touch points.

10. The apparatus of claim 1, wherein:
    the object is a blood vessel, and
    the one or more processors operate to determine the in-plane orientation of the intravascular image with respect to the blood vessel in the intravascular image.

11. The apparatus of claim 1, wherein the one or more processors operate to determine the in-plane orientation of the intravascular image with respect to a pullback direction at the determined acquisition location.

12. A method for controlling, viewing and/or updating one or more imaging modalities in a display, the method comprising:
    obtaining an angiography image of an object;
    obtaining an intravascular image at an acquisition location that is within at least a portion of the object, wherein the angiography image is obtained before the obtaining of the intravascular image, after the obtaining of the intravascular image, or simultaneously with the obtaining of the intravascular image;
    displaying an image for each of multiple imaging modalities on a display, the multiple imaging modalities including at least an imaging modality for the intravascular image and an imaging modality for the angiography image;
    determining the acquisition location of the intravascular image in the object within the angiography image;
    determining an in-plane orientation of the intravascular image based on the intravascular image and the angiography image and based on a curvature by selecting one of a manual in-plane orientation determining and an automatic in-plane orientation determining, the in-plane orientation being a rotational orientation of the intravascular image in a plane that is vertical to a co-registration path and/or a longitudinal direction of the object, wherein the manual and/or automatic determining of the in-plane orientation uses: (i) information of the curvature and information of one or more side branches of the object, or (ii) information of the curvature, information of one or more side branches of the object, and a target of or in the object and a location of the target for a boundary condition;
    in a case where the manual in-plane orientation determining is selected, using the manual in-plane orientation determining by receiving a manually input rotation angle number and/or selecting an input rotation angle that is used to place an intravascular frame on the co-registration path or a co-registration path plane, and using or receiving a manually input frame number to change the display to show an intravascular frame corresponding to the manually input frame number for performance of the in-plane orientation determining, and/or, in a case where the automatic in-plane orientation determining is selected, using the automatic in-plane orientation determining by performing the in-plane orientation determining automatically based on the intravascular image and the angiography image and based on the curvature;
    registering the intravascular image to the angiography image based on the determined acquisition location and the determined in-plane orientation; and
    changing or updating the display for each of the multiple imaging modalities based on the in-plane orientation information and/or based on a request to update or change the in-plane orientation.

13. The method of claim 12, further comprising one or more of the following:
    co-registering the obtained angiography image and the obtained intravascular image;
    co-registering the obtained angiography image and an obtained Optical Coherence Tomography (OCT) or Intravascular Ultrasound (IVUS) image;
    determining whether a Percutaneous Coronary Intervention (PCI) is needed for the object;
    in a case where it is determined that the object needs the PCI, performing the PCI, obtaining one or more additional angiography and/or intravascular images, and performing the determining of the acquisition location, the determining of the in-plane orientation, and the registering for the one or more additional angiography and/or intravascular images, or, in a case where it is determined that the object does not need the PCI, saving the images;
    in a case where the PCI is to be performed, planning the PCI;
    in a case where the PCI is performed, assessing or evaluating procedural success of the PCI;
    evaluating the physiology of the object; and/or
    in a case where the object is a vessel or blood vessel, evaluating the physiology of the vessel and/or a lesion of the vessel.

14. The method of claim 12, wherein the object is a blood vessel, and the acquisition location is a region that is diseased and/or is a region that a physician(s), clinician(s) or other user(s) is/are considering for further assessment.

15. The method of claim 12, further comprising one or more of the following:
    co-registering the obtained angiography image and the obtained intravascular image, and obtain one or more additional angiography and/or intravascular images, wherein the obtained intravascular image and/or the obtained one or more additional intravascular images include an obtained one or more Optical Coherence Tomography (OCT) or Intravascular Ultrasound (IVUS) images or frames;

obtaining information from the one or more OCT or IVUS images or frames of one or more of the following: a type of the target and the location of the target where the target is a plaque, a lumen shape and/or a lumen size, and one or more side branches of the object, wherein the object is a blood vessel;

determining the in-plane orientation of each OCT or IVUS frame using information of the curvature, the one or more side branches, and a lumen shape and/or size based on information from both one or more OCT or IVUS images or frames and angiography image or images;

constructing or reconstructing a three-dimensional (3D) structure of the object; and/or using the constructed or reconstructed 3D structure for one or more of visualization, Percutaneous Coronary Intervention (PCI) planning, PCI performance, and physiological assessment.

16. The method of claim 15, further comprising one or more of the following:

determining OCT or IVUS frame orientation relative to the co-registration path using side branch location information relative to a main branch or a predetermined branch of the blood vessel;

displaying an option to perform the construction or reconstruction of a 3D structure on the display;

displaying buttons, choices or options to select one of the manual in-plane orientation determining and the automatic in-plane orientation determining;

in a case where the manual in-plane orientation determining is selected, using the manual in-plane orientation determining by receiving a manually input rotation angle number and/or selecting an input rotation angle that is used to place an OCT or IVUS frame on the co-registration path or the co-registration path plane, and using or receiving a manually input frame number to change the display to show the OCT or IVUS frame corresponding to the manually input frame number for performance of the in-plane orientation determination; and/or in a case where the automatic in-plane orientation determining is selected, using the automatic in-plane orientation determining by performing the in-plane orientation determining automatically based on the intravascular image or the obtained one or more Optical Coherence Tomography (OCT) or Intravascular Ultrasound (IVUS) images or frames and based on the angiography image or images.

17. The method of claim 12, wherein one or more of the following: (i) wherein the multiple imaging modalities include two or more of the following: a modality for a tomography image; a modality for an Optical Coherence Tomography (OCT) image; a modality for an auto-fluorescence image; a modality for a fluorescence image; a modality for a near-infrared auto-fluorescence (NIRAF) image; a modality for a near-infrared auto-fluorescence (NIRAF) image in a predetermined view, a carpet view, and/or an indicator view; a modality for a near-infrared fluorescence (NIRF) image; a modality for a near-infrared fluorescence (NIRF) image in a predetermined view, a carpet view, and/or an indicator view; a modality for a three-dimensional (3D) rendering; a modality for a 3D rendering of a vessel; a modality for a 3D rendering of a vessel in a half-pipe view or display; a modality for a 3D rendering of the object; a modality for a lumen profile; a modality for a lumen diameter display; a modality for a longitudinal view; computer tomography (CT); Magnetic Resonance Imaging (MRI); Intravascular Ultrasound (IVUS); a modality for an X-ray image or view; and a modality for an angiography view; and/or wherein the multiple imaging modalities include three or more of the following: a modality for a tomography image; a modality for an OCT image; a modality for a fluorescence image; a modality for an auto-fluorescence image; a modality for a near-infrared auto-fluorescence (NIRAF) image; a modality for a near-infrared auto-fluorescence (NIRAF) image in a predetermined view, a carpet view, and/or an indicator view; a modality for a near-infrared fluorescence (NIRF) image; a modality for a near-infrared fluorescence (NIRF) image in a predetermined view, a carpet view, and/or an indicator view; a modality for a 3D rendering; a modality for a 3D rendering of a vessel; a modality for a 3D rendering of a vessel in a half-pipe view or display; a modality for a 3D rendering of the object; a modality for a lumen profile; a modality for a lumen diameter display; a modality for a longitudinal view; CT; MRI; IVUS; a modality for an X-ray image or view; and a modality for an angiography view.

18. The method of claim 12, further comprising one or more of the following:

(i) receiving information for an interventional device to be used for a Percutaneous Coronary Intervention (PCI); and/or (ii) in a case where the interventional device is a stent, performing one or more of: detecting stent expansion or underexpansion, detecting stent apposition or malapposition, performing co-registration, performing imaging, displaying a notification regarding the detected stent expansion or underexpansion, and displaying a notification regarding the detected stent apposition or malapposition.

19. The method of claim 12, further comprising one or more of the following:

(i) employing information on a two-dimensional (2D) and/or three-dimensional (3D) structure or structures for the object to create or construct/reconstruct a computational fluid dynamics (CFD) model or result for the object;

(ii) using 2D or 3D results and/or 2D or 3D structure(s) and calculating fractional flow reserve (FFR) and/or instantaneous wave-free ratio (iFR);

(iii) employing CFD to calculate one or more pressures and to have or obtain the FFR and/or the iFR;

(iv) calculate the FFR and provide information on treatment option(s) for the treatment of stenosis and/or another medical condition;

(v) using the FFR and/or the iFR in real-time;

(vi) calculating pressure(s) and including a lamp parameter/circuit analog model;

(vii) including or using an Optical Coherence Tomography (OCT) or Intravascular Ultrasound (IVUS) images or frames FFR method that uses anatomic information; and/or (viii) including or using an Optical Coherence Tomography (OCT) or Intravascular Ultrasound (IVUS) images or frames FFR method that uses anatomic information, wherein the anatomic information includes at least a volume of a vessel.

20. The method of claim 12, wherein:
the object is a blood vessel, and
the method further comprises determining the in-plane orientation of the intravascular image with respect to the blood vessel in the intravascular image.

21. The method of claim 12, further comprising determining the in-plane orientation of the intravascular image with respect to a pullback direction at the determined acquisition location.

22. A non-transitory computer-readable storage medium storing at least one program for causing a computer to execute a method for controlling, viewing and/or updating one or more imaging modalities in a display, the method comprising:
obtaining an angiography image of an object;
obtaining an intravascular image at an acquisition location that is within at least a portion of the object, wherein the angiography image is obtained before the obtaining of the intravascular image, after the obtaining of the intravascular image, or simultaneously with the obtaining of the intravascular image;
displaying an image for each of multiple imaging modalities on a display, the multiple imaging modalities including at least an imaging modality for the intravascular image and an imaging modality for the angiography image;
determining the acquisition location of the intravascular image in the object within the angiography image;
determining an in-plane orientation of the intravascular image based on the intravascular image and the angiography image and based on a curvature by selecting one of a manual in-plane orientation determining and an automatic in-plane orientation determining, the in-plane orientation being a rotational orientation of the intravascular image in a plane that is vertical to a co-registration path and/or a longitudinal direction of the object, wherein the manual and/or automatic determining of the in-plane orientation uses: (i) information of the curvature and information of one or more side branches of the object, or (ii) information of the curvature, information of one or more side branches of the object, and a target of or in the object and a location of the target for a boundary condition;
in a case where the manual in-plane orientation determining is selected, using the manual in-plane orientation determining by receiving a manually input rotation angle number and/or selecting an input rotation angle that is used to place an intravascular frame on the co-registration path or a co-registration path plane, and using or receiving a manually input frame number to change the display to show an intravascular frame corresponding to the manually input frame number for performance of the in-plane orientation determining, and/or, in a case where the automatic in-plane orientation determining is selected, using the automatic in-plane orientation determining by performing the in-plane orientation determining automatically based on the intravascular image and the angiography image and based on the curvature;
registering the intravascular image to the angiography image based on the determined acquisition location and the determined in-plane orientation; and
changing or updating the display for each of the multiple imaging modalities based on the in-plane orientation information and/or based on a request to update or change the in-plane orientation.

* * * * *